United States Patent [19]

Brain et al.

[11] 3,966,718

[45] June 29, 1976

[54] 7-β-ACYLAMINO-CEPH-3-EMS AND SALTS AND ESTERS THEREFOR

[75] Inventors: Edward George Brain, Leigh, Nr. Reigate; Neal Frederick Osborne, West Croydon, both of England

[73] Assignee: Beecham Group Limited, Great Britain

[22] Filed: Jan. 17, 1974

[21] Appl. No.: 434,137

[30] Foreign Application Priority Data

Jan. 18, 1973   United Kingdom................ 2561/73

[52] U.S. Cl........................... 260/243 C; 260/239 A; 260/290 HL; 260/294.8 R; 260/295 R; 260/327 P; 260/309.7; 60/332.2 A; 260/471 R; 260/471 C; 260/468 H; 260/468 R; 260/558 H; 424/246

[51] Int. Cl.².............. C07D 501/50; C07D 501/52; C07D 501/54; C07D 501/56

[58] Field of Search................................. 260/243 C

[56] References Cited

UNITED STATES PATENTS

| | | | |
|---|---|---|---|
| 3,225,038 | 12/1965 | Flynn.............................. | 260/243 C |
| 3,352,858 | 11/1967 | Crast et al....................... | 260/243 C |
| 3,449,338 | 6/1969 | Flynn.............................. | 260/243 C |

*Primary Examiner*—Raymond V. Rush
*Assistant Examiner*—David E. Wheeler

[57] ABSTRACT

Antimicrobially active substituted ceph-3-ems, procedure for their preparation and intermediates for use in the procedure are described. These cephalosporins are characterized by having a 2- or 3- pyridyl group attached to the carbon atom of the methylene group in the 3-position by a carbon-carbon bond and not a carbon-nitrogen bond.

9 Claims, No Drawings

7-β-ACYLAMINO-CEPH-3-EMS AND SALTS AND ESTERS THEREFOR

This invention relates to a novel class of antimicrobially active substituted ceph-3-ems, to a process for their preparation and to intermediates useful in their preparation. The antimicrobially active substituted ceph-3-ems of this invention have, in general, activity against Gram-positive organisms, and many have activity against both Gram-positive and Gram-negative organisms.

The ceph-3-em nucleus is depicted in formula (I) below and is conventionally numbered as shown:

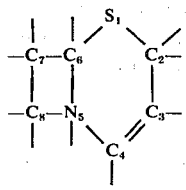
(I)

The numeral 3 in the term "ceph-3-em" refers to the position of the double bond. If the double bond had been located between $C_2$ and $C_3$ in formula (I) the nucleus would have been that of a ceph-2-em.

According to the present invention there is provided a 7-β-acylamino-ceph-3-em of formula (II) or a pharmaceutically acceptable acid addition salt thereof;

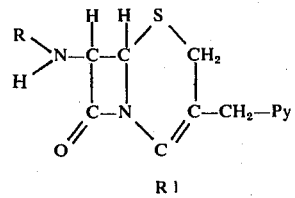
(II)

wherein Py represents a 2- or 3- pyridyl group or quaternised 2- or 3- pyridyl group, R represents an organic acyl group and $R^1$ represents a carboxylic acid group or a pharmaceutically acceptable salt or ester of a carboxylic acid group.

The presence of the 2- or 3- pyridyl group in compounds of formula (II) allows the formation of acid addition salts. Such salts include, for example, inorganic salts such as the sulphate, nitrate, phosphate, borate and hydrohalides e.g. hydrochloride, hydrobromide and hydroiodide, and organic salts such as the acetate, oxalate, tartrate, malate, citrate, succinate, benzoate, ascorbate and methanesulphonate. Quaternised pyridyl groups Py in compounds (II) include the methiodide and metho-trifluoroacetete.

The group $R^1$ in compounds of formula (II) is a carboxylic acid group or a pharmaceutically acceptable salt or ester of a carboxylic acid group. Examples of suitable salts include the sodium, potassium, calcium, magnesium or aluminium salts, and ammonium or substituted ammonium salts for example those with trialkylamines such as triethylamine, procaine, dibenzylamine, triethanolamine. 1-ephenamine, ethylpiperidine and other amines which have been used to form salts with benzylpenicillin. Examples of suitable esters include those which break down readily in the human body to leave the parent acid, e.g. acyloxy alkyl esters such as acetoxymethyl, pivaloyloxymethyl, α-acetoxyethyl, α-acetoxybenzyl and α- pivaloyloxyethyl esters. Other suitable esters include lactone, thiolactone and diethiolactone esters (i.e. compounds of formula (II) wherein $R^1$ is a group of formula

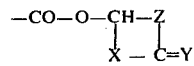

wherein X and Y are oxygen or sulphur and Z is a divalent hydrocarbon goup) especially the phthalide and substituted phthalide esters, e.g. 3,4-dimethylphthalide ester.

The group R in formula (II) has been defined as an organic acyl group. The vast majority of antimicrobially active ceph-3-ems which have been reported to date in the literature carry a 7-acylamino group. It has been found over the years that by varying the identity of the 7-acylamino group, the spectrum and/or level of antibacterial activity of any given ceph-3-em can be modified. Similarly, in the present case, for any given Py group in formula (II) a very large number of 7-acylamino groups can be introduced, producing a range of compounds of widely differing spectra and levels of activity. In general, however, whatever the identity of the acyl group R, the compounds of formula (II) possess some activity and those who are familiar with the cephalosporin art will be aware of the range of acyl groups R which may be introduced.

In general therefore, R in formula (II) may be any of the organic acyl groups which are present in the reported natural and semi-synthetic penicillins and cephalosporins. Examples include acyl groups of the following general formulae (i), (ii) and (iii):

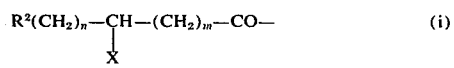
(i)

wherein $R^2$ represents hydrogen or an alkyl, cycloalkyl (especially $C_3$ to $C_6$ cycloalkyl), cycloalkenyl (especially cyclohexenyl or cyclohexadienyl), aryl (especially phenyl or substituted phenyl e.g. p-hydroxy-phenyl), heterocyclic (e.g. thienyl, pyridyl, substituted isoxazolyl such as 3-0-chlorophenyl-5-methyl isoxazol-4-yl, sydnonyl, tetrazolyl); X represents hydrogen, a hydroxy group, a halogen atom (especially chlorine), a carboxylic acid group or carboxylic acid ester group (e.g. a phenyl or indanyl ester), an azido group, an amino group or substituted amino group, (including ureido, substituted ureido, guanidino and substituted guanidino groups), a triazolyl group, a tetrazolyl group, a cyano group, an acyloxy group (e.g. formyloxy or lower alkanoyloxy group) or an esterified hydroxy group; and $n$ and $m$ each separately represent 0, 1, 2 or 3.

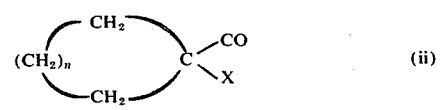
(ii)

wherein $n$ is an integer from 1 to 4 and X is as defined in (i) above.

wherein $R^4$ is an alkyl, aralkyl, aryl (especially phenyl or substituted phenyl group), cycloalkyl (especially a $C_3$ to $C_6$ cycloalkyl or substituted cycloalkyl group), cycloalkenyl (especially a cyclohexenyl or cyclohexadienyl group) or a heterocyclic group (especially a thienyl or pyridyl group); $R^5$ and $R^6$ are each hydrogen lower alkyl, phenyl, benzyl or phenylethyl groups; and Z is oxygen or sulphur.

Specific examples of organic acyl groups R which may be present in the compounds of this invention include 2-thienylacetyl, phenylacetyl, 2-hydroxyphenylacetyl, 2-aminophenylacetyl, 4-pyridylacetyl, 2-amino-p-hydroxyphenylacetyl and 1-tetrazolylacetyl, but other acyl groups are specifically exemplified in the Examples later in this specification.

The compounds of formula (II) may be prepared by a process which comprises reacting a compound of formula (III), or a salt or silyl derivative thereof.

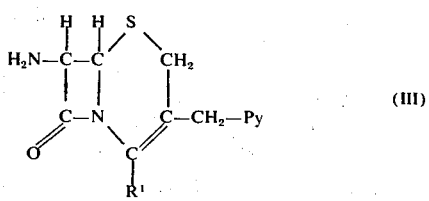

wherein $R^1$ is a carboxylic acid group or a salt or ester of a carboxylic acid group and Py is a 2- or 3- pyridyl group, with an activated N-acylating derivative of the appropriate acid ROH, R being an acyl group in which any free amino or hydroxy groups may be blocked and, if a silyl derivative of compound (III) was employed, thereafter removing the silyl group by hydrolysis or alcoholysis, and optionally converting any protected amino or hydroxy group to free amino or hydroxy groups, and optionally quaternising the pyridyl group.

By the term "silyl derivative" of compound (III) we mean the product of the reaction between compound (III) and a silylating agent such as a halodialkylsilane, a halotrialkylsilane, a halodialkoxysilane or a halotrialkoxysilane, or a corresponding aryl or aralkyl silane and compounds such as hexamethyldisilazane. The silyl derivatives of compound (III) are extremely sensitive to moisture and hydroxylic compounds, and, after, reaction with the N-acylating derivative of the acid ROH, the silyl groups of the intermediate acylated compound can be removed by alcoholysis or hydrolysis.

Suitable N-acylating derivatives of the acid ROH include the acid chloride, bromide, anhydride, mixed anhydrides and the reactive intermediates formed from the acid and a carbodiimide or a carbonyldiimidazole. Any reactive groups such as amino groups or hydroxy groups which are present in the acyl group R may be protected during the course of the N-acylation. Suitable protecting groups for amino groups are known from the literature on the synthesis of α-aminobenzyl penicillins or α-aminobenzyl cephalosporins. For example, any amino groups may be blocked by protonation, by conversion to tertbutoxycarbonylamino groups or to N-methoxycarbonylpropen-2-ylamino groups. Such protecting groups may subsequently be removed to leave the free amino group. A useful way of protecting a free hydroxy group is to use the appropriate dicarboxylic anhydride e.g. mandelic and carboxanhydride. After N-acylation with this reagent the free hydroxy group is generated without the need for deprotection.

Since they are useful intermediates in the preparation of the compounds of formula (II), this invention also includes compounds of formula (III) i.e. the following compounds and their salts and esters:

3-(2-pyridylmethyl)-7-β-amino-cephem-4-carboxylic acid.
3-(3-pyridylmethyl)-7-β-amino-3-cephem-4-carboxylic acid.

It is sometimes possible to prepare compounds of formula (II) by a process which comprises heating a compound of formula (IV) or (IVA)

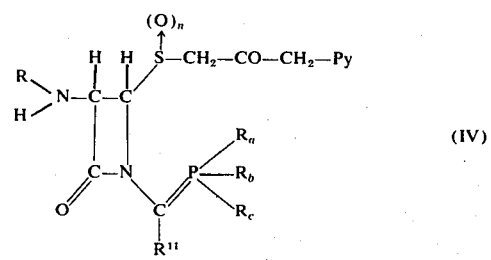

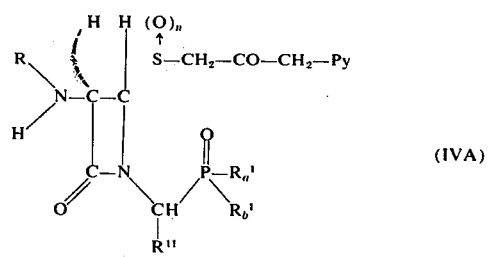

wherein R, and Py are as defined in formula (II), $n$ is 0 or 1, $R''$ is an esterified carboxylic acid group, $R_a$, $R_b$ and $R_c$ are substituted or unsubstituted lower alkyl, aryl or aralkyl groups, and $R_a{}^1$ and $R_b{}^1$ are substituted or unsubstituted alkoxy or aralkoxy groups, said heating step being carried out at a temperature of from 30°C to 150°C in an inert organic solvent, and, if a compound of formula (IV) or (IVA) wherein $n = 1$ was employed, subsequently reducing the resultant sulphoxide to a sulphide, and, if desired, de-esterifying the esterified carboxylic acid group $R''$ to produce a free carboxylic acid group or a salt thereof. Preferably the temperature of the heating step is from 75°C to 125°C.

Suitable solvents are those which are inert under the reaction conditions and which boil between 30° and 150°C e.g. dioxan, toluene and benzene. High boiling solvents are difficult to remove after the reaction and are therefore not preferred. For a clean reaction it may be preferable to carry the heating step out under an inert atmosphere, although this is not essential. In addition it is preferable to dry the solvent thoroughly to avoid any decomposition of the starting material.

The radicals $R_a$, $R_b$ and $R_c$ in the phosphine compound of formula (IV) may be optionally substituted lower alkyl or aryl (preferably phenyl) radicals, and the radicals $R_a^1$ and $R_b^1$ in compound (IVA) may be optionally substituted lower alkoxy radicals.

If necessary, the sulphoxide compound which results after cyclising (IV) or (IVA) ($n=1$) may be reduced to the desired sulphide by any of the conventional methods, e.g. those described in British Pat. No. 1280693. One such method which we have found particularly useful is treatment with triphenylphosphine and acetylchloride.

The above described method of preparing compound (II) by cyclisation of the Wittig reagents (IV) and (IVA) is only applicable where the acyl group R is sufficiently stable to survive the sometimes prolonged heating step and any subsequent de-esterification reaction intended to convert group R'' to a carboxylic acid group.

dine. The compounds of this invention have advantages over the most closely related prior art compounds in that, (comparing the compound of this invention with its closest prior art analogue) they tend to have a broader spectrum of activity and/or enhanced level of activity against clinically important organisms. In many cases there is evidence from work in mice that the compounds of this invention give rise to more prolonged blood levels than their closest prior art analogues.

The following Examples illustrate this invention:

EXAMPLE 1

A. Preparation of tert butyl-3-(3-pyridylmethyl)-7β-(2-thienylacetamido)-3-cephem-4-carboxylate

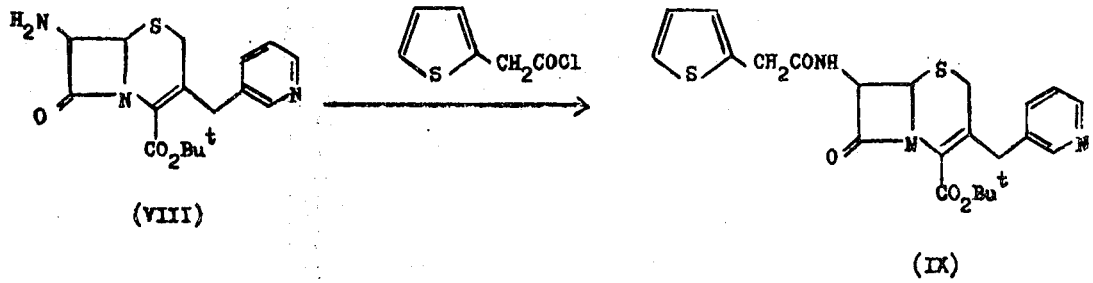

(N.B. If R in (IV) or (IVA) is a blocking group such as triphenylmethyl which, after completion of the bicyclic system (II) can be removed by conventional means, then the free amino compound (III) can be prepared, and then acylated as described previously).

It will, of course, be recognized that the compounds of this invention are closely related structurally to the known ceph-3-em of formula (V) — approved name "cephaloridine."

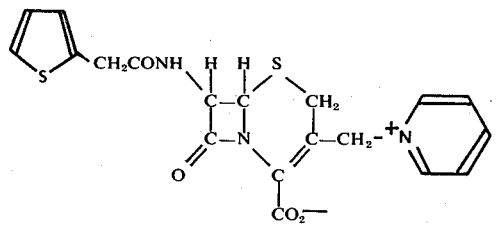

The compounds of this invention differ from cephaloridine in that the Py group in formula (II) is attached to the methylene group by a carbon-carbon bond, not a carbon-nitrogen bond. Compounds of formula (II) are not accessible by the routes used to prepare cephalori- To a stirred solution of the crude free base (VIII) (75 mg) in dry methylene chloride at $-10°$ was added triethylamine (65 mg) and 2-thieylacetyl chloride (freshly distilled, 39 mg). The mixture was stirred at $-10°$ for 15 minutes, diluted with methylene chloride (10 ml) and washed with brine. The dried ($MgSO_4$) organic layer was evaporated to give a crude gum.

The crude gum was chromatographed on silica gel eluting with ethyl acetate/petroleum ether mixtures to give the desired cephem (IX) as a solid foam (34 mg, 45%).

$\nu_{max}$ cm$^{-1}$ ($CHCl_3$) 1780, 1715, 1685.

Molecular ion measured at 471.1269 ($C_{23}H_{25}N_3O_4S_2$ requires 471.1286, Error = 3.6 ppm). Fragmentation was consistent with structure.

$\lambda_{max}$ (ethanol) 237.5 nm (13,500). 263 (10,650):
$\alpha_D^{23} = 83.9°$ (C = 1% in $CHCl_3$)

δppm $CDCL_3$): 1.52 (s, 9H), 2.96 and 3.42 (AB quartet, 2H, J=18Hz), 3.41 and 4.09 (AB quartet, 2H, J = 15Hz), 3.85 (s, 2H), 4.98 (d, 1H, J=5Hz) 5.85 (dd, 1H, J=5Hz, J'=9Hz), 6.8–7.9 (aromatic multiplet + NH), 8.2–8.8 (broad, aromatics).

B. Preparation of 3-(3-pyridylmethyl)-7β-(2-thienylacetamido)-3-cephem-4-carboxylic acid trifluoroacetate salt

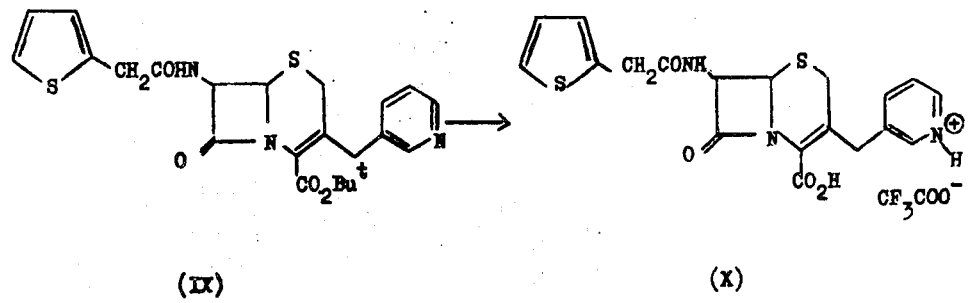

The cephem (IX) (33 mg) was dissolved in trifluoroacetic acid (0.5 ml) and the solution was kept at room temperature for 5 minutes. The solution was evaporated and the residual gum re-evaporated from dry toluene (4 × 1 ml). The residual gum was triturated with dry ether to give the desired carboxylic acid trifluoroacetate salt (X) as a solid (25 mg, 68%).

$\nu_{max}$cm$^{-1}$ (Nujol) 1780, 1670 (broad).

The minimum inhibitory concentration (MIC) of this compound require to inhibit the growth of five typical Gram-positive bacteria are tabulated below:

| Organism | MIC ($\mu$g/ml in agar) |
|---|---|
| B Subtilis | 0.25 |
| Staph-aureus Oxford | 0.05 |
| Staph-aureus Russell | 10.0 |
| β haemolytic Strep CN10 | 0.1 |
| Strep pneumoniae CN33 | 0.1 |

PREPARATION OF STARTING MATERIAL FOR EXAMPLE

A. Preparation of 1-(1-benzyloxycarbonyl-2-methyl-1-propeny)-3-(triphenylmethylamino)-4-[3-(3-pyridyl)prop-2-ynylthio]azetidin-2-one.

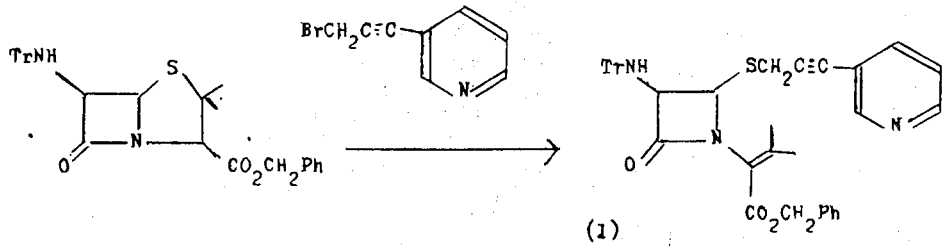

(1)

Benzyl 6-β-(triphenylmethylamino)pencillanate (1.1 g.) was stirred under nitrogen in dry tetrahydrofuran (40 ml) containing 1-bromo-3-(3-pyridyl)prop-2-yne hydrobromide (0.61 g., 1.1 eg., obtained from 3-ethynylpyridine by successive reaction with ethyl magnesium bromide, formaldehyde and finally phosphorus tribromide). A 0.778M solution of potassium t-butoxide in t-butenol (5.7 ml. diluted with 10 ml. tetrahydrofuran) was added over 30 mins. and stirring was continued for 2 hours. The reaction mixture was evaporated (in vacuo) to a small volume and ethyl acetate added. The organic phase was washed with water and brine, dried (Na$_2$ SO$_4$) and evaporated to dryness. The residue was chromatographed on silica, eluting with ethyl acetate/light petroleum (1:9,2 liters to give an amorphous product (0.187 g.) 14%.

$\nu_{max}$ (CHCl$_3$) 1755 cm$^{-1}$ (β-lactam), 1715 cm$^{-1}$ (enter). 6 ppm (CDCl$_3$) 2.02 (s, 3H), 2.18 (s,3H), 2.8–3.1 (m, 3H) exchanging 1H with D$_2$O) 4.8–5.25 (m,2H, 5.3 (s, 2H) 6.9–8.8 (aromatic multiplet).

B. Preparation of 4-[3(3-pyridyl)-prop-2-ynylthio]-3-triphenylmethylamino-azetidin-2-one

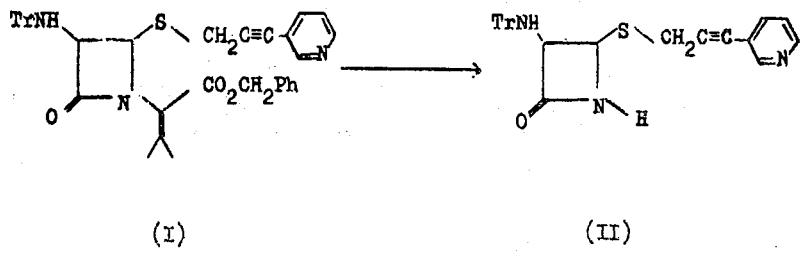

The β-lactam (I) (3.5 g) was dissolved in a mixture of pyridine (50 ml) and water (5 ml). The stirred mixture was cooled in an ice-salt bath and treated with finely powdered potassium permanganate (1.25 g). The cooled mixture was stirred for a further 1 hour. The mixture was diluted with ethyl acetate (300 ml) and brine (100 ml) and filtered through Kieselguhr. The organic layer was separated and washed with brine. The dried (MgSO$_4$) organic layer was evaporated to give a crude gum (3.1 g).

The crude gum was chromatographed on silica gel eluting with ethyl acetate/petroleum ether mixtures to give the desired β-lacttam (II) as a solid foam (0.751 g, 30%).

$\nu_{max}$ cm$^{-1}$ (CHCl$_3$) 3380, 1765.

δppm (CDCl$_3$) 3.25 (s, 3H, 1H exchanges with D$_2$O); 4.60 (broad s, 2H); 6.61 (s, 1H) exchanges with D$_2$O); 7.0 – 8.8 (Aromatics).

C. Preparation of 1-(1-hydroxy-1-tert-butoxycarbonylmethyl)-4-[3-(3-pyridyl)-prop-2-ynylthio]-3-triphenylmethylaminoacetidin-2-one

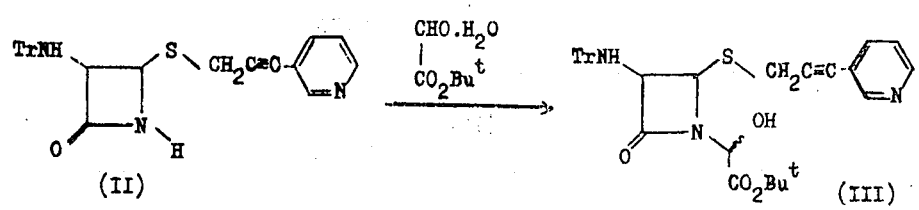

Tert-butyl glyoxalate monohydrate (1.93 g) and dry benzene (20 ml) were refluxed under nitrogen in a Dean and Stark apparatus until all the water had been removed. The β-lactam (II) (620 mg) was added and the mixture refluxed under nitrogen for a further 3 hours. The reaction mixture was cooled and washed with water (5 × 10 ml). The dried (MgSO₄) organic layer was evaporated to give a crude gum (1.45 g).

The crude gum was chromatographed on silica gel eluting with ethyl acetate/petroleum ether mixtures to give the desired β-lactam (III) a mixture of stereoisomers as a solid foam (510 mg, 65%).

$\nu_{max}$ cm$^{-1}$ (CHCl₃) 1775, 1740.

δppm (CDCl₃) 1.48 (s, 9H); 3.17 (s) and 3.37 (s) superimposed on a broad signal (together integrating for 3H, the broad signal exchanges with D₂O to leave two singlets); 3.95 (broad s, 1H, exchanges with D₂O); 4.40 – 4.85 (m, 2H); 5.13 and 5.25 (2 singlets together integrating for 1H); 7.0 – 8.7 (Aromatics).

D. Preparation of 1-(1-chloro-1-tert-butoxycarbonylmethyl)-4-[3-(3-pyridyl)-prop-2-ynylthio]-3-triphenylmethylaminoazetidin-2-one

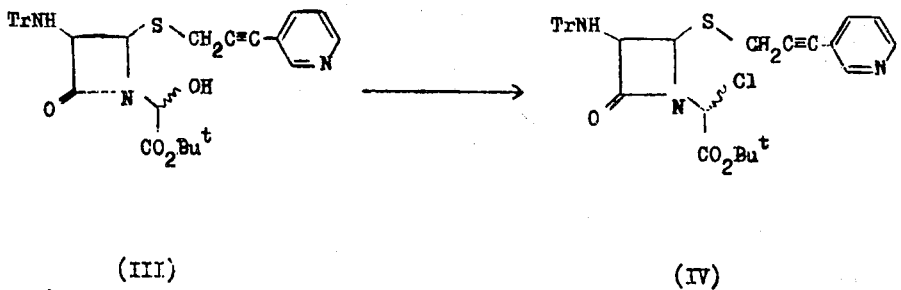

(III)                                    (IV)

The β-lactam (III) (515 mg) was dissolved in a mixture of dry tetrahydrofuran (5 ml) and dry dioxan (5 ml) and the resulting mixture was cooled to −5°C to −10°C. Dry pyridine (202 mg) was added followed by purified thionyl chloride (304 mg) dropwise in 3 minutes. The resulting mixture was stirred at 0° to −5°C for 15 minutes. The mixture was filtered and the residue washed with dry toluene. The combined filtrates were evaporated and the residual gum extracted with dry toluene (4 × 19 ml). The combined extracts were filtered and evaporated to give a gum. Re-evaporation of the gum from dry ether gave the desired chloride (IV) as a solid foam (436 mg, 82%).

$\nu_{max}$ cm$^{-1}$ (CHCl₃) 1780, 1745.

E. Preparation of 4-[3-(3-pyridyl)-prop-2-ynylthio]-1-(1-tert-butoxycarbonyl-1-triphenylphosphoranylidenemethyl)-3-triphenylmethylamino-azetidin-2-one

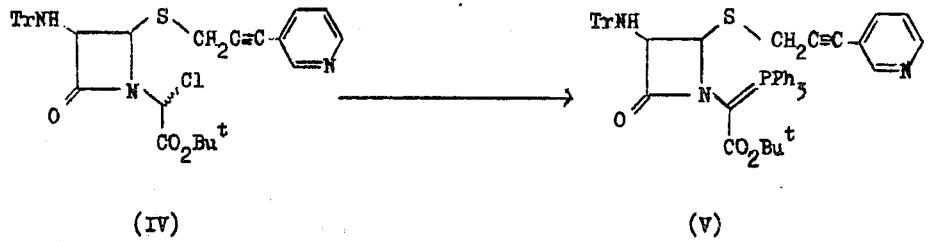

(IV)                                    (V)

The chloride (IV) (436 mg), triphenyl phosphine (368 mg), and 2,6-dimethylpyridine (90 mg) were stirred at 50°C in dry dioxan (10 ml) under nitrogen for 5 hours. The mixture was cooled, diluted with ethyl acetate (100 ml) and washed with brine. The dried (MgSO₄) organic layer was evaporated to give a brown gum (727 mg).

The gum was chromatographed on silica gel eluting with ethyl acetate/petroleum ether mixtures to give the desired phosphorane (V) as a solid foam (262 mg, 44%).

$\nu_{max}$ cm$^{-1}$ (CHCl₃) 1755, 1640.

Preparation of 4-[3-(3-pyridyl)-2-oxopropylthio]-1-(1-tert-butoxycarbonyl-1-triphenylphosphoranylidonemethyl)-3-triphenylmethylamino-azetidin-2-one

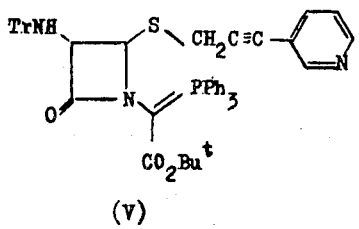 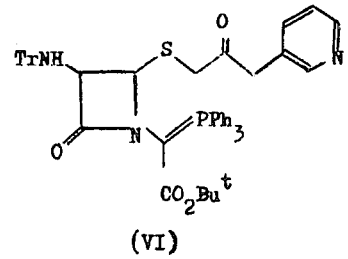

(V)                                    (VI)

The phosphorane (V) (250 mg) was refluxed in piperidine (5 ml) under nitrogen for 3 hours. The mixture was evaporated and the residual gum dissolved in ethyl acetate. The solution was shaken with N/10 HCl (20 ml) for 5 minutes, basified with saturated NaHCO₃ solution and the organic layer separated. The aqueous layer was re-extracted with ethyl acetate. The combined extracts were washed with brine, dried (MgSO₄), and evaporated to give a crude foam (250 mg).

The crude foam was chromatographed on silica gel eluting with ethyl acetate/petroleum ether mixtures to give the desired keto-phosphorane (VI) as a solid foam (197 mg, 77%). $\nu_{max}$ cm$^{-1}$ (CHCl₃) 1750, 1650.

G. Preparation of tert-butyl-3-(3-pyridylmethyl)-7-triphenylmethylamino-3-cephem-4-carboxylate The cephem (VII) (1.0g.) was dissolved in acetone (10 ml.), cooled to 0°C and treated with p-toluene sulphonic acid monohydrate (710 mg.). The mixture was allowed to attain room temperature and was maintained at this temperature for 2 hours. The mixure was evaporated and the resulting gum was shaken with ethyl acetate (25 ml) and saturated sodium bicarbonate solution (10 ml). The organic layer was separated and the aqueous layer was re-extracted with ethyl acetate (2 × 10 ml). The combined extracts were washed with brine, dried (NgSO₄) and evaporated to give a crude gum (0.96 g.). The crude gum was chromatographed on silica gel eluting with ethyl acetate/pe-

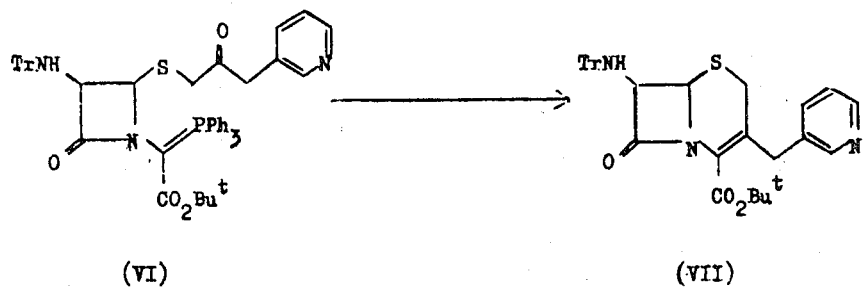

(VI)        (VII)

The keto-phosphorane (VI) (197 mg) was refluxed in dry dioxan (5 ml) under nitrogen for 8 hours. The mixture was evaporated to give a crude gum.

The crude gum was chromatographed on silica gel eluting with ethyl acetate/petroleum ether mixtures to give the desired cephem (VII) as a solid foam (95 mg, 71%).

$\nu_{max}$ cm$^{-1}$ (CHCl₃) 1775, 1715.

δ ppm (CDCl₃) 1.52 s, 9H); 3.03 (centre of multiplet, 3H, collapsing to AB quartet, 2H, J = 18 Hz with D₂O); 3.70 (centre of AB quartet, 2H, J = 15Hz); 4.31 (d, 1H, J = 5Hz); 4.75 (centre of multiplet, 1H, collapsing to a doublet, J = 5Hz with D₂O); 7.0 - 8.7 (Aromatics, 19H).

After crystallisation from methanol the product had m.p. 169°-171°, $\alpha_D^{23}$ = 13.8° (C = 1% in CHCl₃), $\lambda_{max}$ (ethanol) 263 mm (ε = 10,500).

H. Preparation of tert-butyl 7β-amino-3(3-pyridylmethyl)-3-cephem-4 carboxylate troleum ether mixtures to give the desired free amine (VIII) as a solid foam (0.423 g., 72%).

$\nu_{max}$ (CHCl₃) 1775 cm$^{-1}$, 1715 cm$^{-1}$. Molecular ion measured at 347.1292 (C₁₇H₂₁n₃O₃S requires 347.1303, Error = 3.2 ppm). δ ppm (CDCl₃): 1.55 (s, 9H); 2.7 (broad, 2H, exchanges with D₂O); 3.02 and 3.48 (AB quartet, 2H, J = 18Hz); 3.44 and 4.08 (AB quartet, 2H, J =15Hz); 4.76 (d, 1H, J =5Hs); 4.99 (d, 1H, J = -5Hz); 7.0–8.8 (aromatic multiplet).

EXAMPLE 2

Preparation of 3(3-pyridylmethyl)-7β-(2-thienylacetamido)-3-cephem-4-carboxylic acid The product isolated in Example 1 as the trifluoroacetate salt may also be obtained as the zwitter-ion as follows:

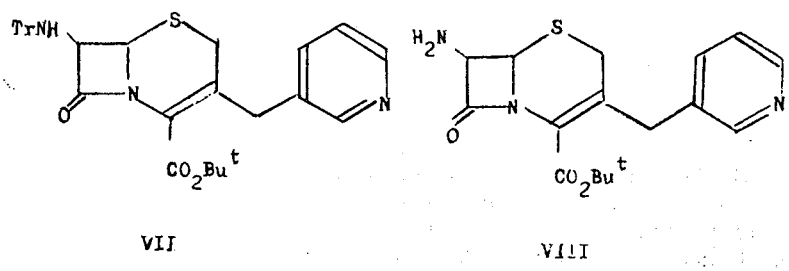

VII        VIII

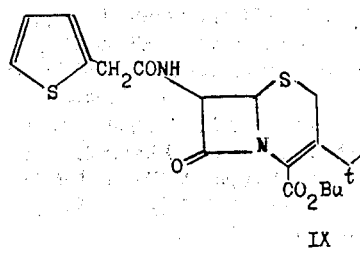
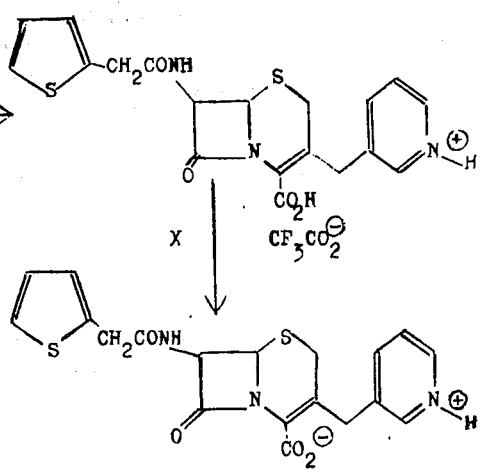

The cephem ester (IX) (179 mg.) was dissolved in trifluoroacetic acid (2 ml.) and was kept at room temperature for 5 minutes. The solution was evaporated and the residual gum re-evaporated from dry toluene (4 × 1 ml.). The residual gum was triturated with dry ether to give the carboxylic acid trifluoroacetate salt (X) as a solid (188 mg.).

The salt (X) (188 mg.) was dissolved in water (40 ml.) and the pH of the resulting solution was adjusted to 5 with triethylamine. The solution was evaporated to dryness and then resulting solid was triturated with water (5 ml.). The solid was collected and dried under vacuum to give the desired cephem (XI) as a white solid (55 mg. 35%). MP= 168°–171°C. $\nu_{max}$ (Nujol) 1765 cm$^{-1}$, 1665 cm$^{-1}$. $\alpha_{max}$ = 238 nm (ethanol) $\epsilon_{max}$=13,200 and 264 nm $\epsilon_{max}$=10,150.

The antibacterial activity of this product was essentially similar to the trifluoroacetate salt described in Example 1.

acetate/petroleum ether mixtures to give the desired cephem (XII) as a solid foam (318 mg., 66%). Crystallisation of the product from ethyl acetate/petroleum ether gave a white crystalline solid.

MP.=157°–9°C. $\nu_{max}$ (CHCl$_3$) 1780 cm$^{-1}$, 1715 cm$^{-1}$, 1680 cm$^{-1}$. $\lambda_{max}$=264 nm (ethanol) $\epsilon_{max}$=11,400. $\alpha_D^{23}$ = −133.1° (C=1% in chloroform). Molecular ion measured at 481.1701 (C$_{25}$H$_{27}$N$_3$O$_5$S requires 481.1671, Error= 6.2 ppm).

δ ppm (CDCl$_3$); 1.57 (s, 9H); 2.99 and 3.45 (AB quartet, 2H, J=18Hz); 3.37 and 4.18 (AB quartet, 2H, J=15 Hz); 4.5–5.4 (broad, 1H), exchanges with D$_2$O); 5.05 (d, 1H, J=5Hz); 5.20 (s, 1H); 5.80 (dd, 1H, J=5Hz, J'=10Hz collapses to d, J=5Hz with D$_2$O); 7.0–8.8 (m, 10H, 1H, exchanges with D$_2$O).

B. Preparation of 7β(D-α-hydroxyphenylacetamido)-3(3-pyridylmethyl)-3-cephem-4-carboxylic acid trifluoroacetate salt.

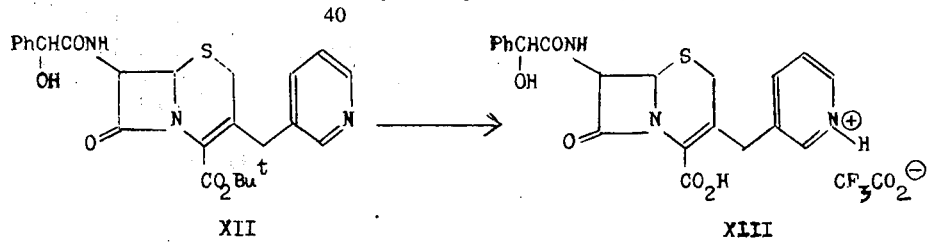

EXAMPLE 3

A. Preparation of tert-butyl '7β(D-α-hydroxyphenylacetamido)-3(3-pyridylmethyl)-3-cephem-4-carboxylate

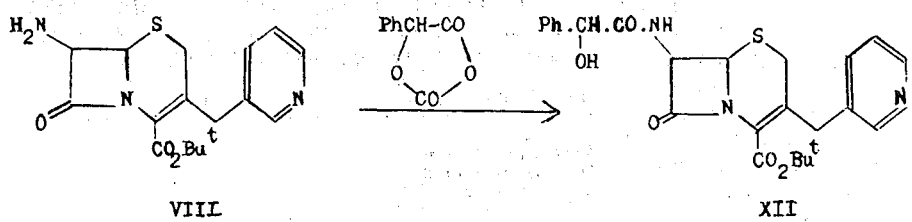

The free amine (VIII) (347 mg.) was dissolved in dry methylene chloride (20 ml.) and cooled to −20°C. To the cooled, stirred solution was added D-mandelic acid carboxyanhydride (196 mg.) portionwise in 5 minutes. The mixture was stirred at −20°C for a further 2 hours and evaporated to give a crude gum. The crude gum was chromatographed on silica gel eluting with ethyl The cephem ester (XII)(150 mg.) was dissolved in trifluoroacetic acid (2 ml.) and was kept at room temperature for 5 minutes. The solution was evaporated and the residual gum was re-evaporated from dry toluene (4 × 1ml.). The residual gum was triturated with dry other to give the desired cephem trifluoroacetate salt (XIII) as a solid (161 mg., 100%).

$\nu_{max}$ (KBr) 1770 cm$^{-1}$, 1670 cm$^{-1}$ (broad). $\lambda_{max}$ = 261 nm (ethanol) $\epsilon_{max}$= 10,350 $\alpha_D^{24}$ = −83.5° (C=1% in ethanol).

The minimum inhibitory concentration (MIC) of this compound required to inhibit the growth of various bacteria on nutrient agar are tabulated below:

| Gram-positive bacteria | MIC (µg/ml) |
|---|---|
| B. subtilis | 0.12 |
| Staph aureus Oxford | 0.25 |
| Staph aureus Russell | 12.5 |
| β-Haemolytic Strep. CN10 | 0.25 |
| Strep. pneumoniae | 0.5 |

| Gram-negative bacteria | MIC (µg/ml) |
|---|---|
| E coli NCTC10418 | 2.5 |
| Salmonella typhi | 2.5 |
| Shigella sonnei | 2.5 |
| Klebsiella aerogenes A | 2.5 |
| Proteus mirabilis C977 | 5.0 |

$\nu_{max}$ (CHCl$_3$) 1780 cm$^{-1}$, 1710 cm$^{-1}$ (broad). $\lambda_{max}$= 264 nm (ethanol) $\epsilon_{max}$= 10,500. $\alpha_D^{24}$= −83.6° (C=1% in chloroform). Molecular ion measured at 580.2358 (C$_{30}$H$_{36}$N$_4$O$_6$S requires 580.2355, Error <1 ppm).

δ ppm (CDCl$_3$): 1.40 (s) and 1.52 (s) (together integrating for 18H); 2.82 and 3.32 (AB quartet, 2H, J=18Hz); 3.29 and 4.07 (AB quartet, 2H, J=15Hz); 4.94 (d, 1H, J=5Hz); 5.30 (d, 1H, J=7Hz); 5.65–6.10 (m, 2H); 7.0–8.9 (aromatic m + NH).

B. Preparation of 7β(D-α-aminophenylacetamido)-3(3-pyridylmethyl)-3-cephem-4-carboxylic acid di-trifluoroacetate salt.

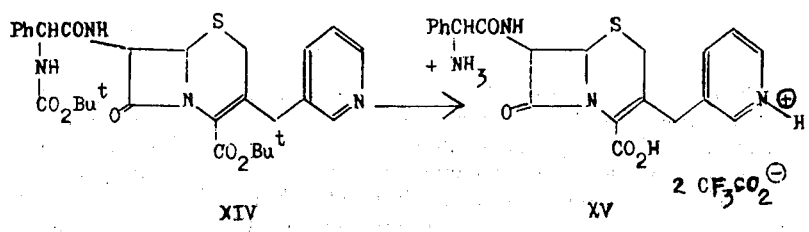

XIV        XV

EXAMPLE 4

A. Preparation of tert-butyl 7β(D-α-tert-butoxycarbonylaminophenylacetamido)-3(3-pyridylmethyl)-3-cephem-4-carboxylate.

The cephem ester (XIV) (80 mg.) was dissolved in rifluoroacetic acid (2 ml.) and was kept at room temperature for 5 minutes. The solution was evaporated and the residual gum was re-evaporated from dry toluene (4 × 1 ml.). The residual gum was triturated with

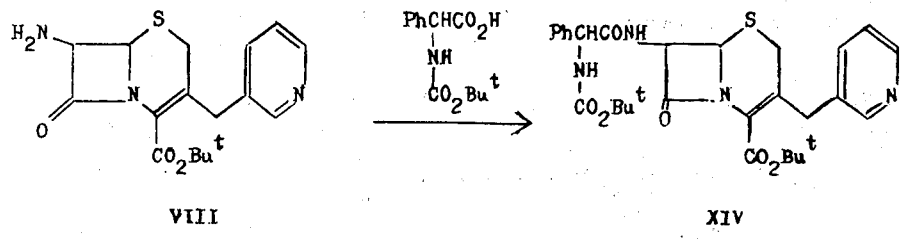

VIII        XIV

To a solution of methyl chloroformate (60 mg.) in dry tetrahydrofuran at −10°C was added dropwise with stirring over a period of 5 minutes a solution containing N(-tert-butoxycarbonyl)-D-α-phenylglycine (159 mg.), dry triethylamine (64 mg.) and N,N-dimethylbenzylamine (1 drop) in dry tetrahydrofuran (5 ml.). The mixture was stirred for a further 25 minutes at −10°C. The free amine (VIII) (200 mg.) in dry tetrahydrofuran (3 ml.) was added dropwise in 5 minutes and the resulting mixture was stirred for a further 2 hours at −10°C. The mixture was filtered and the filtrate evaporated to give a gum. The gum was dissolved in ethyl acetate and washed with saturated sodium bicarbonate solution followed by brine. The dried (MgSO$_4$) organic layer was evaporated to give a crude foam. The crude foam was chromatographed on silica gel eluting with ethyl acetate/petroleum ether mixtures to give the desired cephem ester (XIV) as a solid foam (167 mg., 50%).

dry ether to give the desired cephem di-trifluoroacetate salt (XV) as a solid (76 mg., 84%).

$\nu_{max}$ (KBr) 1775 cm$^{-1}$, 1670 cm$^{-1}$ (broad). $\lambda_{max}$= 264 nm (ethanol) $\epsilon_{max}$=11,050 $\alpha_D^{24}$= −18.5° (C=1% in ethanol).

The minimum inhibitory concentration (MIC) of this compound required to inhibit the growth of various bacteria on nutrient agar are tabulated below:

| Gram-positive bacteria | MIC (µg/ml) |
|---|---|
| B. subtilis | 0.25 |
| Staph. aureus Oxford | 0.25 |
| Staph. aureus Russell | 2.5 |
| βHaemolytic Strep. CN10 | 0.25 |
| Strep. pneumoniae CN33 | 0.5 |

| Gram-negative bacteria | MIC (µg/ml) |
|---|---|
| E coli NCTC 10418 | 2.5 |
| Salmonella typhi | 1.25 |
| Shigella sonnei | 2.5 |
| Klebsiella aerogenes A | 2.5 |
| Proteus mirabilis C977 | 5.0 |

EXAMPLE 5

A. Preparation of tert-butyl 7β(D-α-hydroxyphenylacetamido)-3(3-pyridylmethyl)-3-cephem-4-carboxylate methiodide.

| Gram-positive bacteria | MIC (μg/ml) |
|---|---|
| B. subtilis | 0.25 |
| Staph. aureus Oxford | 0.12 |
| Staph. aureus Russell | 5.0 |
| β-Haemolytic Strep. CN10 | 0.02 |
| Strep. pneumoniae CN33 | 0.12 |

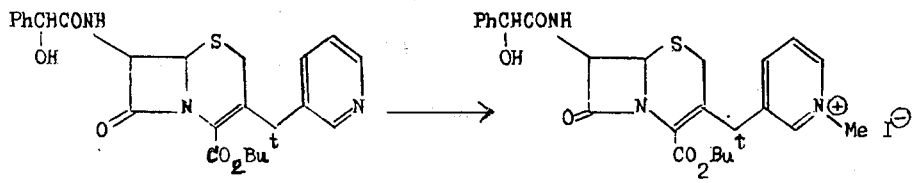

XII    XVI

The cephem ester (XII) (150 mg.) was dissolved in dry tetrahydrofuran (1 ml.) and was treated with methyl iodide (0.2 ml.). The mixture was kept at room temperature for 16 hours. The mixture was diluted with dry ether to give a gum which on trituration with dry ether gave the desired methiodide (XVI) as a yellow amorphous solid (160 mg., 82%).

$\nu_{max}$ (CHCl$_3$) 1780 cm$^{-1}$, 1705 cm$^{-1}$, 1680 cm$^{-1}$. $\lambda_{max}$= 266 nm (ethanol) $\epsilon_{max}$= 11,600, $\alpha_D^{24}$= −139.0° (C=1% in chloroform).

| Gram-negative bacteria | MIC (μg/ml) |
|---|---|
| E coli NCTC10418 | 50 |
| Salmonella typhi | 50 |
| Shigella sonnei | 50 |
| Klebsiella aerogenes A | 50 |
| Proteus mirabilis C977 | 125 |

EXAMPLE 6

A. Preparation of tert-butyl-7β(α-phenoxycarbonylphenylacetamido)-3(3-pyridylmethyl)-3-cephem-4-carboxylate

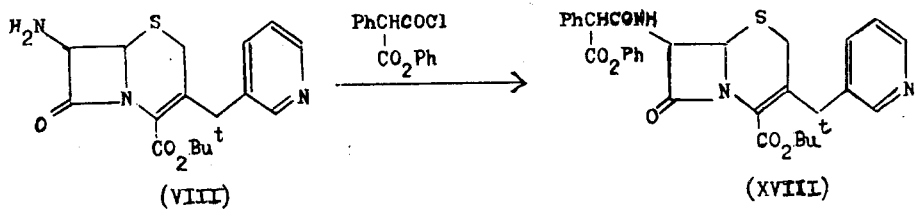

(VIII)    (XVIII)

B. Preparation of 7β(D-α-hydroxyphenylacetamide)-3(3-pyridylmethyl)-3-cephem-4-carboxylic acid metho-trifluoroacetate The free amine (VIII) (200 mg) was dissolved in dry methylene chloride (5 ml.). The solution was cooled to −10°C and treated with dry triethylamine (116 mg.) followed by α-phenoxy-carbonyl phenylacetyl chloride

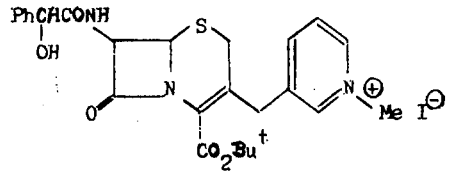  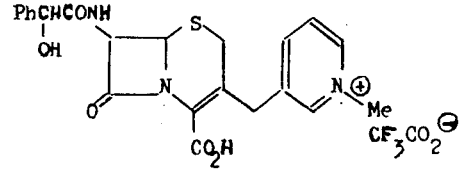

XVI    XVII

The methiodide (90 mg.) was dissolved in trifluoroacetic acid (2 ml.) and kept at room temperature for 5 minutes. The solution was evaporated and the residual gum re-evaporated from dry toluene (4 × 1 ml.). The residual gum was triturated with dry ether to give the desired metho-trifluoroacetate (XVII) as a solid (80 mg., 100%).

$\nu_{max}$ (KBr) 1770 cm$^{-1}$, 1670 cm$^{-1}$ (broad). $\lambda_{max}$= 265 nm (ethanol) $\epsilon_{max}$= 9,550.

The minimum inhibitory concentration (MIC) of this compound required to inhibit the growth of 5 typical gram-positive bacteria on nutrient agar are tabulated below.

(238 mg. obtained by treatment of monophenyl phenylmalonate with thionyl chloride) in dry methylene chloride (2 ml.) dropwise with stirring in 3 minutes. The mixture was stirred at −10°C for 45 minutes. The mixture was diluted with methylene chloride, washed with brine, dried (MgSO$_4$), and evaporated to give a crude gum (410 mg.).

The crude gum was chromatographed on silica gel eluting with ethyl acetate/petroleum ether mixtures to give the desired cephem ester (XVIII) as a solid foam (224 mg., 66%).

$\nu_{max}$ (CHCl$_3$) 1785 cm$^{-1}$, 1740 cm$^{-1}$, 1715 cm$^{-1}$, 1685 cm$^{-1}$.

δ ppm (CDCl₃): 1.52 (s, 9H); 2.95 and 3.40 (AB quartet, 2H, J=18 Hz); 3.31 and 4.09 (AB quartet, 2H, J=15Hz); 4.87 and 4.89 (2 singlets together integrating for 1H); 5.00 (d, 1H, J=5Hz); 5.88 (dd, 1H, J=5Hz, J'=9Hz); 6.9–8.9 (Aromatic multiplet + NH). $\epsilon_{max}$=

EXAMPLE 7

A. Preparation of Tert-butyl-7β(D-α-tert-butoxycarbonylamino-phenylacetamido)-3(2-pyridylmethyl)-3-cephem-4-carboxylate

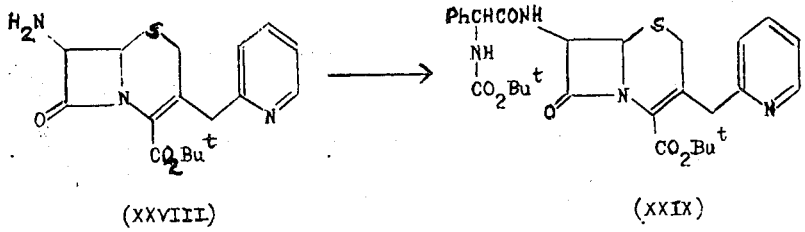

(XXVIII)                                           (XXIX)

263 nm (ethanol) $\epsilon$= 11,200. $\alpha_D^{23}$= −66.9% (C=1% in chloroform).

B. Preparation of 7β(α-phenoxycarbonylphenylacetamido)-3(3-pyridylmethyl)-3-cephem-4-carboxylic acid trifluoroacetate

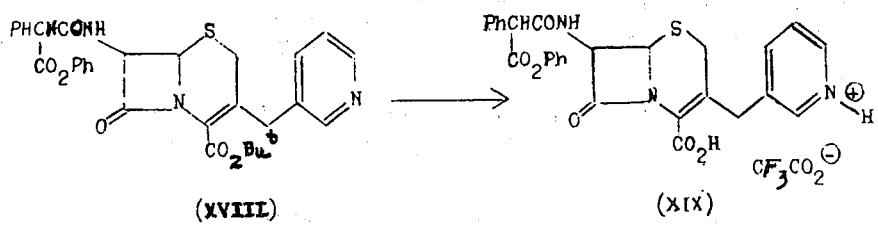

(XVIII)                                    (XIX)

The cephem ester (XVIII) (100 mg.) was dissolved in trifluoroacetic acid (2 ml.) and kept at room temperature for 5 minutes. The solution was evaporated and the residual gum was re-evaporated from dry toluene (4 × 1 ml.). The residual gum was triturated with dry ether to give the desired trifluoroacetate salt (XIX) as a solid (98 mg. 89%).

$\nu_{max}$ (KBr) 1770 cm⁻¹, 1670 cm⁻¹ (broad). $\lambda_{max}$=263.5 nm (ethanol) $\epsilon$=11,300. $\alpha_D^{23}$= −1.8° (C=1% in ethanol).

The minimum inhibitory concentrations (MIC) of this compound required to inhibit the growth of various bacteria on nutrient agar are tabulated below:

| Gram-positive bacteria | MIC (μg/ml) |
|---|---|
| B. subtilis | 12.5 |
| Staph. aureus Oxford | 5 |
| Staph. aureus Russell | 25 |
| β-Haemolytic Strep. CN10 | 12.5 |

| Gram-negative bacteria | MIC (μg/ml) |
|---|---|
| E coli NCTC 10418 | 50 |
| Salmonella typhi | 125 |
| Shigella sonnei | 12.5 |
| Proteus mirabilis C977 | 25 |

To a solution of methyl chloroformate (60 mg.) in dry tetrahydrofuran (5 ml.) cooled to −10°C was added dropwise in 5 minutes with stirring a solution containing N-(tert-butoxycarbonyl)-Dα-phenyl glycine (159 mg.), triethylamine (64 mg.) and N,N-dimethylbenzylamine (1 drop) in dry tetrahydrofuran (5 ml.). After 25 minutes the free amine (XXVIII) (200 mg.) in dry tetrahydrofuran (3 ml.) was added dropwise in 5 minutes. The mixture was stirred at −10°C for a further 2 hours. The mixture was filtered and the filtrate was evaporated to give a gum which was dissolved in ethyl acetate and washed with saturated NaHCO₃ solution and brine. The dried (MgSO₄) organic layer was evaporated to give a crude foam (380 mg).

The crude foam was chromatographed on silica gel eluting with ethyl acetate/petroleum ether mixtures to give the desired cephem ester (XXIX) as a solid foam (325 mg., 97%).

$\nu_{max}$. (CHCl₃) 1780 cm⁻¹, 1710 cm⁻¹, 1690 cm⁻¹ (shoulder).

δ ppm (CDCl₃): 1.40 (s, 9H); 1.50 (s, 9H); 3.39 (s, 2H); 3.69 and 4.20 (AB quartet, 2H, J=15Hz); 4.83 (d, 1H, J=5Hz); 5.24 (d, 1H, J=7Hz); 5.60–6.00 (m, 2H); 6.80–8.70 (Aromatic multiplet + NH). Molecular ion measured at 580.2370 (C₃₀H₃₆N₄O₆S requires 580.2355, Error = 2.6 ppm). $\lambda_{max}$=264.5 nm (ethanol) $\epsilon$= 13,800 and $\lambda_{max}$ =270 nm $\epsilon$=14,000. $\alpha_D^{23}$= −86.7° (C=1% in chloroform).

B. Preparation of 7β(Dα-aminophenylacetamido)-3(2-pyridylmethyl)-3-cephem-4-carboxylic acid di-trifluoroacetate

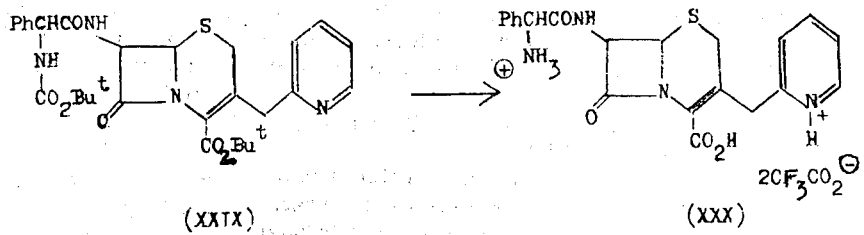

(XXIX)                                          (XXX)

The cephem ester (XXIX) (100 mg.) was dissolved in trifluoroacetic acid (2 ml.) and was kept at room temperature for 5 minutes. The solution was evaporated and the residual gum was re-evaporated from dry toluene (4 × 1 ml.). The residual gum was triturated with dry ether to give the desired cephem trifluoroacetate salt (XXX) as a solid (98 mg., 88%).

$\nu_{max}$ (KBr) 1775 cm$^{-1}$, 1670 cm$^{-1}$ (broad). $\lambda_{max}$ =264 nm (ethanol). $\epsilon$=12,300 and $\lambda_{max}$ =270 nm $\epsilon$= 12,300. $\alpha_D^{23}$= —9.0° (C= 1% in ethanol).

The minimum inhibitory concentrations (MIC) of this compound required to inhibit the growth of various bacteria on nutrient agar are tabulated below:

| Gram-positive bacteria | MIC (μg/ml) |
| --- | --- |
| B. subtilis | 1.25 |
| Staph. aureus Oxford | 1.25 |
| Staph. aureus Russell | 12.5 |
| β-Haemolytic Strep. CN10 | 1.25 |

| Gram-negative bacteria | MIC (μg/ml) |
| --- | --- |
| E coli NCTC 10418 | 50 |
| Salmonella typhi | 12.5 |
| Shigella sonnei | 25 |
| Proteus mirabilis C977 | 125 |

PREPARATION OF STARTING MATERIAL FOR EXAMPLE 7

A. Preparation of 1(1-benzyloxycarbonyl-2-metyl-1-propenyl)-3(triphenylmethyamino)-4[3(2-pyridyl)prop-2-ynylthio]-azetidin-2-one

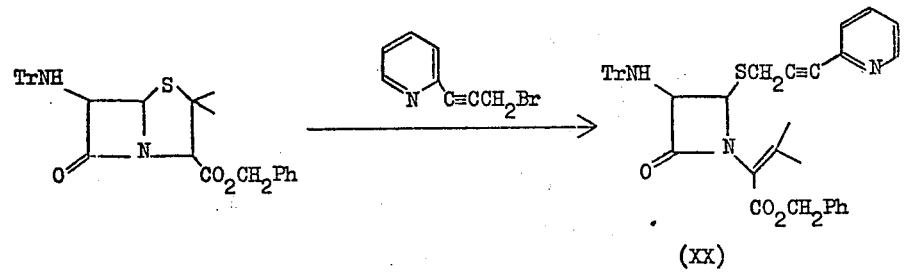

Benzyl 6-β-(triphenylmethylamino)penicillanate (146 g.) was stirred in dry tetrahydrofuran (1500 ml.) containing 1-bromo-3(2-pyridyl)-prop-2-yne hydrobromide (81.4 g., obtained from 2-ethynylpyridine by successive reaction with ethyl magnesium bromide, formaldehyde and finally phosphorus tribromide) and powdered sodium hydroxide (23.4 g.) for 24 hours at room temperature.

The mixture was filtered and the filtrate was evaporated to give a residual gum. The residual gum was dissolved in ethyl acetate and was washed with brine. The dried (MgSO$_4$) organic layer was evaporated to give a crude gum.

The crude gum was chromatographed on silica gel eluting with ethyl acetate/petroleum ether mixtures to give the desired seco-compound (XX) as a solid foam (81.4 g., 46%).

$\nu_{max}$ (CHCl$_3$) 1760 cm$^{-1}$, 1720 cm$^{-1}$. δ ppm (CDCl$_3$): 2.02 (s, 3H); 2.18 (s, 3H); 3.04 (centre of AB quartet, J-15Hz, superimposed on a broad signal, together integrating for 3H, the broad signal exchanged with D$_2$O); 4.3–4.8 (m, 2H, collapsing to two doublets, J=5Hz with D$_2$O); 4.90 (s, 2H); 7.0–8.7 (Aromatic multiplet).

B. Preparation of 1[3(2-pyridyl)prop-2-ynylthio]-3-triphenylmethylaminoazetidin-2-one

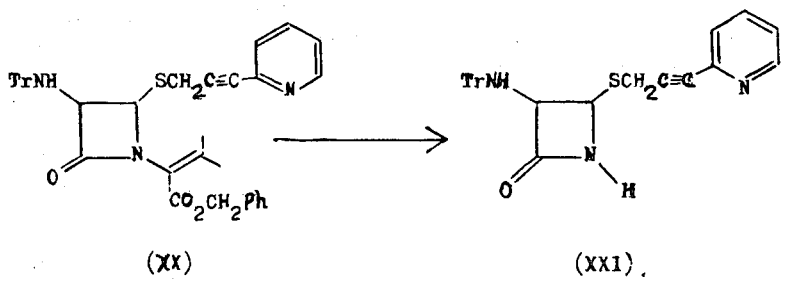

The seco-compound (XX) (105 g.) was dissolved in a mixture of pyridine (1000 ml.) and water (100 ml.). The stirred mixture was cooled in an ice-salt bath and treated with finely powdered potassium permanganate (37.6 g.) portionwise in 1 hour. The cooled mixture was stirred for a further 1 hour. The mixture was diluted with ethyl acetate (1000 ml.) and brine (200 ml.) and filtered through Kieselguhr. The organic layer was separated and washed with brine. The dried MgSO$_4$) organic layer was evaporated to give a crude gum.

The crude gum was chromatographed on silica gel eluting with ethyl acetate/petroleum ether mixtures to give the desired β-lactam (XXI) as a solid foam (14.0 g. 18%).

$\nu_{max}$ (CHCl$_3$) 1760 cm$^{-1}$.

δ ppm (CDCl$_3$) 3.05 (broad d, 1H, J=8Hz, exchanges with D$_2$O); 3.31 (s, 2H); 4.50–4.83 (m, 2H); 7.0–8.7 (Aromatic multiplet + NH).

C. Preparation of 1(1-hydroxy-1-tert-butoxycarbonylmethyl)-4-[3(2-pyridyl)prep-2-ynylthio]-3-triphenylmethylaminoazetidin-2-one.

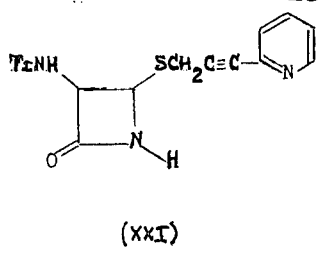
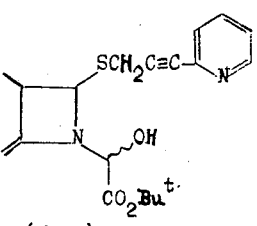

Tert-butyl glyoxalate monohydrate (83 g.) and dry benzene (400 ml.) were refluxed under nitrogen in a Dean and Stark apparatus until all the water had been removed. The β-lactam (XXI) (26.6 g.) was added and the mixture refluxed under nitrogen for a further 2 hours. The mixture was cooled and washed with water (5 × 200 ml.). The dried (MgSO$_4$) organic layer was evaporated to give a crude oil (68g.).

The crude oil was chromatographed on silica gel eluting with ethyl acetate/petroleum ether mixtures to give the desired β-lactam (XXII) a mixture of stereoisomers as a solid foam (14.7 g., 43%).

$\nu_{max}$ (CHCl$_3$ 1765 cm$^{-1}$, 1735 cm$^{-1}$.

D. Preparation of 1(1-chloro-1-tert-butoxycarbonylmethyl)-4-[3(2-pyridyl)prop-2-ynylthio]-3-triphenylmethylamino-azetidin-2-one

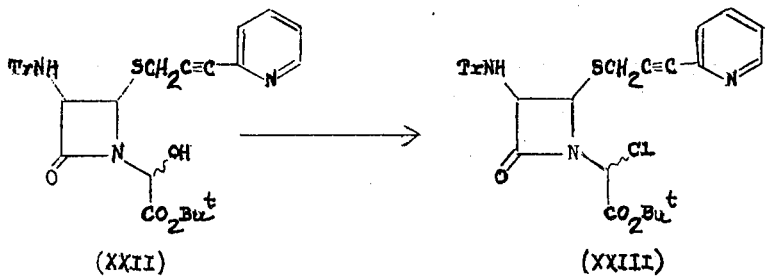

The β-lactam (XXII) (13.7g.) was dissolved in a mixture of dry tetrahydrofuran (100 ml.) and dry dioxan (100 ml.) and the resulting solution was cooled to −5° to −10°C. Re-distilled 2,6-dimethyl pyridine (7.26 g.) was added followed by purified thionyl chloride (8.09 g.) dropwise in 10 minutes. The mixture was stirred at 0° to −5°C for a further 20 minutes. The mixture was diluted with dry toluene (100 ml.) and filtered. The filtrate was evaporated and the residual gum was reevaporated from dry toluene (2 × 100 ml.).

Re-evaporation of the gum from dry ether gave the desired chloride (XXIII), contaminated with some 2,6-dimethylpyridine hydrochloride, as a solid foam (16.0 g.).

$\nu_{max}$ (CHCl$_3$) 1770 cm$^{-1}$, 1740 cm$^{-1}$.

E. Preparation of 4[3(2-pyridyl)prop-2-ynylthio]-1(1-tert-butoxycarbonyl-1-triphenylphosphoranylidenemethyl)-3-triphenylmethylamine-azetidin-2-one

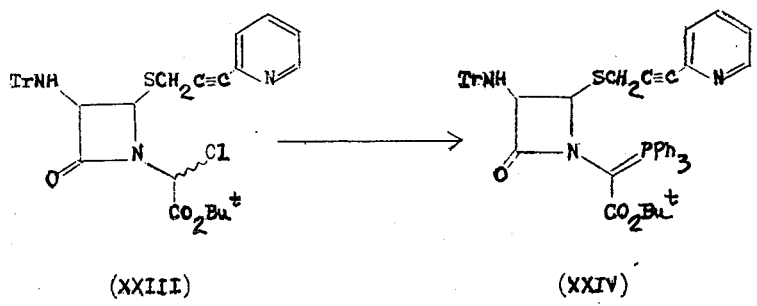

The chloride (XXIII) (16.0 g.), triphenyl phosphine (11.9 g.), and 2,6-dimethyl pyridine (2.6 g.) were stirred at 50°C in dry dioxan (150 ml.) under dry nitrogen for 10 hours. The mixture was cooled, diluted with ethyl acetate (250 ml.) and washed with brine. The dried (MgSO$_4$) organic layer was evaporated to give a crude gum (28.5 g.).

The crude gum was chromatographed on silica gel eluting with ethyl acetate/petroleum ether mixtures to give the desired phosphorane (XXIV) as a brown solid foam (7.82 g., 41%).

$\nu_{max}$ (CHCl$_3$) 1755 cm$^{-1}$, 1625 cm$^{-1}$.

F. Preparation of 4[3(2-pyridyl)-2-oxopropylthio]-1(1-tert-butoxycarbonyl-1-triphenylphosphoranylidenemethyl)-3-triphenylmethylamino-azetidin-2-one

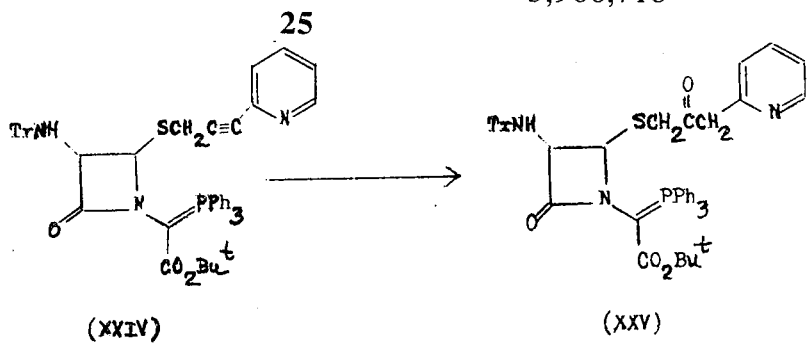

(XXIV) → (XXV)

The phosphorane (XXIV) (7.72 g.) was refluxed in piperidine (100 ml.) under nitrogen for 2 hours. The mixture was evaporated and the residual gum was dissolved in ethyl acetate. The solution was washed with N/10 HCl (3 × 20 ml.) followed by brine. The dried (MgSO$_4$) organic layer was evaporated to give a crude brown foam.

The crude foam was chromatographed on silica gel eluting with ethyl acetate/petroleum ether mixtures to give the keto-phosphorane (XXV) as a dark yellow solid foam (4.90 g., 62%).

$\nu_{max}$ (CHCl$_3$) 1750 cm$^{-1}$, 1635 cm$^{-1}$.

G. Preparation of tert-butyl 3(2-pyridylmethyl)-7β-triphenylmethylamino-3-cephem-4-carboxylate

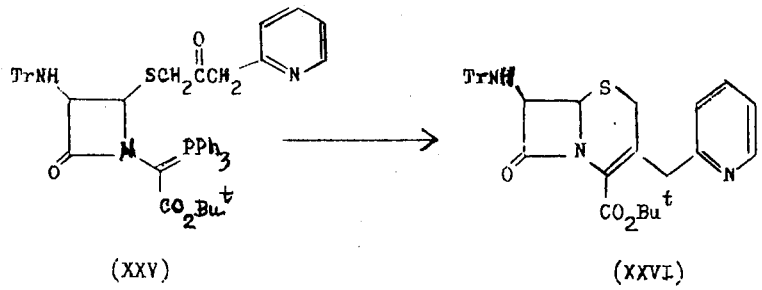

(XXV) → (XXVI)

The keto-phosporane (XXV) (4.90 g.) was refluxed in dry dioxan (50 ml.) under nitrogen for 20 hours. The mixture was evaporated to give a crude gum.

The crude gum was chromatographed on silica gel eluting with ethyl acetate/petroleum ether mixtures to give the desired cephem (XXVI) as a solid foam (2.51g., 75%)

$\nu_{max}$ (CHCl$_3$) 1770 cm$^{-1}$, 1715 cm$^{-1}$. $\lambda_{max}$=263 nm (ethanol) $\epsilon_{max}$=10,500. $\alpha_D^{24}$=+39.6°(C=1% in chloroform).

δ ppm (CDCl$_3$): 1.50 (s, 9H); 2.95 (d, 1H, J=10Hz, exchanges with D$_2$O); 3.21 (s, 2H); 3.61 and 4.16 (AB quartet, 2H, J=15Hz); 4.30 (d, 1H, J=5Hz); 4.50–5.00 (m, 1H); 7.0–8.7 (Aromatic multiplet).

H. Preparation of tert-butyl 7β-amino-3(2-pyridylmethyl)-3-cephem-4-carboxylate

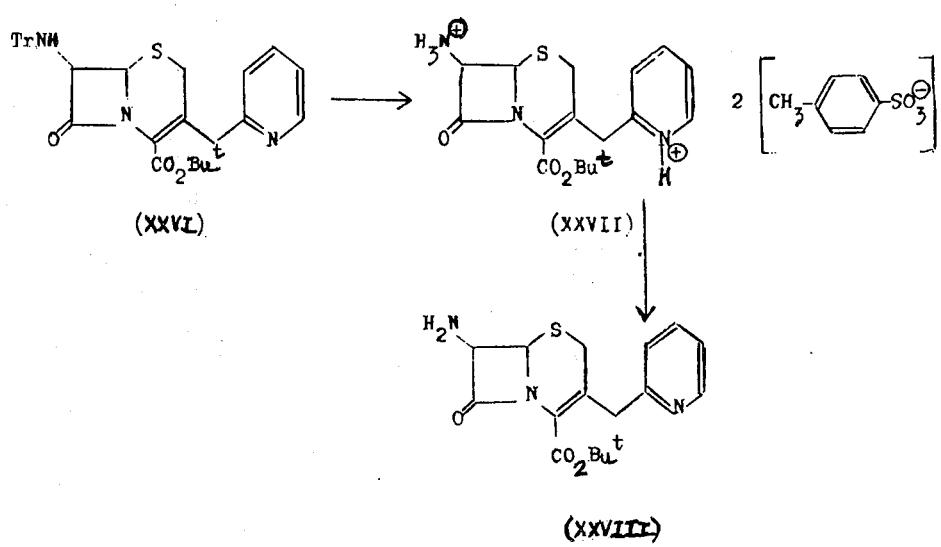

(XXVI) → (XXVII) → (XXVIII)

The cephem (XXVI) (1.0 g.) was dissolved in acetone (10 ml.), cooled to 0°C and teated with p-toluene sulphonic acid monohydrate (710 mg.). The mixture was allowed to attain room temperature and kept at that temperature for 2 hours.

The solid was filtered and washed thoroughly with acetone and dried under vacuum to give the di-p-toluene sulphonic acid salt (XXVII) as a white crystalline solid (519 mg., 44%)

MP= 165°–7°C. $\nu_{max}$ (Nujol) 1800 cm$^{-1}$ 1715 cm$^{-1}$. $\lambda_{max}$=264 nm (ethanol) $\epsilon_{max}$=11,800 and 270 nm $\epsilon_{max}$=11,800. $\alpha_D^{24}$=−26.9° (C=1% in ethanol).

The di-p-toluene sulphonic acid salt (XXVII) (465 mg.) was shaken with ethyl acetate (10 ml.) and saturated sodium bicarbonate solution (10 ml.). The organic layer was separated and the aqueous layer re-extracted with ethyl acetate (2 × 5 ml.). The combined extracts were washed with brine, dried (MgSO₄) and evaporated to give the desired free amine (XXVIII) as a solid foam (224 mg., 96% from the salt.

$\nu_{max}$.(CHCl₃) 1775 cm⁻¹, 1715 cm⁻¹.

B. Preparation of 7β-[D-2-(1-imidazolidonecarbonylamino)-phenylacetamido]-3(3-pyridylmethyl)-3-cephem-4-carboxylic acid trifluoroacetic acid salt

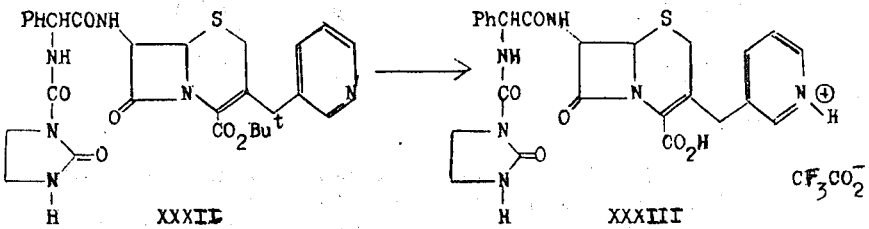

δ ppm (CDCl₃): 1.52 (s, 9H); 1.89 (s, 2H, exchanges with D₂O; 3.47 (s, 2H); 3.69 and 4.22 (AB quartet, 2H, J=15Hz); 4.75 (d, 1H, J=5Hz); 4.99 (d, 1H, J=5Hz); 7.0–8.7 (Aromatic multiplet). Molecular ion measured at 347.1321 (C₁₇H₂₁N₃O₃S requires 347.1304, Error= 4.9 ppm).

EXAMPLE 8

A. Preparation of tert-butyl 7β-[D-2-(1-imidazolidonecarbonylamino)-phenylacetamido]-3(3pyridylmethyl)-3-cephem-4-carboxylate The cephem ester (XXXII) (100 mg.) was dissolved in trifluoroacetic acid (2ml.) and kept at room temperature for 5 minutes. The solution was evaporated and the residual gum was re-evaporated from dry toluene (4 × 1 ml.). The residual gum was triturated with dry ether to give the desired trifluoroacetic acid salt (XXXIII) as a solid (93 mg., 85%).

$\nu_{max}$ (KBr) 1770 cm⁻¹; 1715 cm⁻¹ (broad);1665 cm⁻¹ (broad). $\lambda_{max}$= 263.5 nm (ethanol), $\epsilon$ = 10,800. $\alpha_D^{23}$ = − 28.4° (C= 0.5% in ethanol).

The minimum inhibitory concentration (MIC) of this compound required to inhibit the growth of various

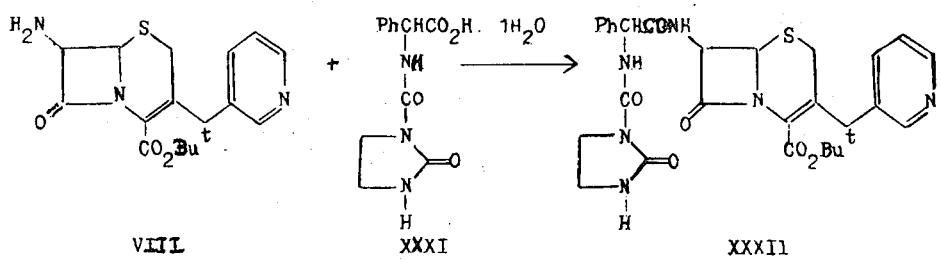

To a mixture of the acid monohydrate (XXXI) (162 mg.) and the free amine (VIII) (200 mg.) in dry tetrahydrofuran (20 ml.) was added with stirring, a solution of dicyclohexylcarbodiimide (119 mg.) in dry tetrahydrofuran (5ml.), dropwise in 3 minutes. The mixture was stirred at room temperature for 3 hours. The mixture was filtered and the solid was washed thoroughly with ethyl acetate. The combined filtrates were evaporated to give a crude foam (371 mg.).

The crude product was chromatographed on silica gel eluting with chloroform/methanol mixtures to give the desired cephem ester (XXXII) as a solid (240 mg., 70%).

$\nu_{max}$ (CHCl₃) 1780 cm⁻¹, 1720 cm⁻¹, 1670 cm⁻¹ (shoulder).

δ ppm. (CDCl₃) 1.53 (s, 9H); 2.9–4.3 (m, 8H); 4.91 (d, 1H, J=5Hz.); 5.6–6.3 (m, 3H, 1H exchanges with D₂O); 7.1–8.2 (m, 8H); 8.51 (broad s, 2H); 9.15–9.45 (m, 1H). $\lambda_{max}$ = 263.5 nm (ethanol), $\epsilon$ = 11,060. $\alpha_D^{23}$ = −64.2° (C=1% in chloroform).

bacteria on nutrient agar are tabulated below:

| Gram-positive bacteria | MIC(μg/ml.) |
|---|---|
| B. subtilis | 1.25 |
| Staph. aureus Oxford | 0.25 |
| Staph. aureus Russell | 12.5 |
| β-Haemolytic Strep CN 10 | 0.12 |
| Strep. pneumoniae CN 33 | 0.25 |

| Gram negative bacteria | MIC (μg/ml) |
|---|---|
| E coli NCTC 10418 | 25 |
| Shigella sonnei | 25 |
| Salmonella typhi | 25 |
| Klebsiella aerogenes A | 12.5 |
| Proteus mirabilis C 977 | 50 |

EXAMPLE 9

A. Preparation of tert-butyl 7β-phenoxyacetamido-3(3-pyridylmethyl)-4-carboxylate

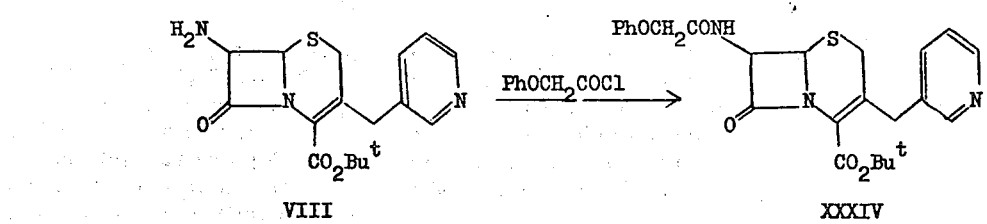

The free amine (200 mg.) was dissolved in dry methylene chloride (5 ml.) and the solution was cooled to −10°C. To the cooled, stirred solution was added triethylamine (116 mg.) followed by phenoxyacetyl chloride (148 mg.) dropwise in 3 minutes. The mixture was stirred at −10°C for a further 30 minutes. The mixture was diluted with methylene chloride (20 ml.), washed with brine, dried (MgSO$_4$), and evaporated to give a foam (328 mg.)

The crude product was chromatographed on silica gel eluting with ethyl acetate/petroleum ether mixtures to give the desired cephem ester (XXXIV) as a solid foam (173 mg., 63%).

$\nu_{max}$ (CHCl$_3$) 1780 cm$^{-1}$, 1710 cm$^{-1}$ (shoulder); 1690 cm$^{-1}$.

δppm (CDCl$_3$) 1.58 (s, 9H); 3.05 and 3.50 (AB quartet, 2H, J=18Hz.); 3.45 and 4.18 (AB quartet, 2H, J=14Hz.); 4.60 (s, 2H); 5.09 (d, 1H, J=5Hz.); 5.96 (dd, 1H, J=5Hz., J'=9Hz.); 6.8–7.9 (m, 8H); 8.6 (broad signal, 2H). Molecular ion measured at 481.1673 C$_{25}$H$_{27}$N$_3$O$_5$S requires 481.1671, Error = 0.4 ppm). $\lambda_{max}$ =263.5 nm (ethanol) ε = 13,000 and $\lambda_{max}$ = 274 nm ε = 13,100. $\alpha_D^{23}$=−90.5° (C=1% in chloroform).

B. Preparation of 7β-phenoxyacetamido-3(3-pyridylmethyl)-3-cephem-4-carboxylic acid trifluoroacetic acid salt

| Gram-positive bacteria | MIC (μg/ml) |
|---|---|
| *B. subtilis* | 0.25 |
| *Staph aureus* Oxford | 0.02 |
| *Staph aureus* Russell | 0.12 |
| β-Haemolytic Strep. CN 10 | 0.12 |
| *Strep. pneumoniae* CN 33 | 0.12 |

| Gram-negative bacteria | MIC (μg/ml) |
|---|---|
| *E coli* NCTC 10418 | 500 |
| *Salmonella typhi* | 500 |
| *Shigella sonnei* | 500 |
| *Klebsiella aerogenes* A | 500 |
| *Proteus mirabilis* C 977 | 125 |

EXAMPLE 10

A. Preparation of tert-butyl 7β-ethylthioacetamido-3(3-pyridylmethyl)-3-cephem-4-carboxylate

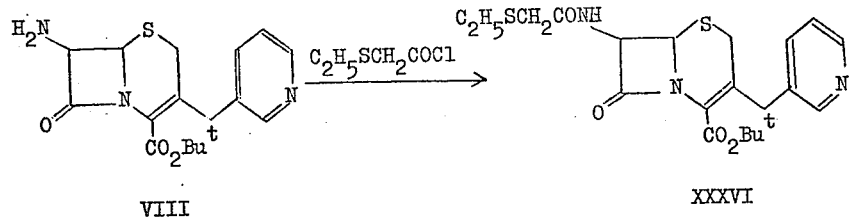

VIII → XXXVI

The free amine (VIII) (240 mg.) was dissolved in dry methylene chloride (5 ml.), cooled to −10°C, and treated with triethylamine (140 mg.) followed by ethyl thioacetyl chloride (144 mg.) dropwise with stirring in 3 minutes. The mixture was stirred at −10°C for a further 30 minutes. The mixture was diluted with ethyl acetate, washed with brine, dried (Mg SO$_4$), and evaporated to give a crude gum.

The crude product was chromatographed on silica gel eluting with ethyl acetate/petroleum ether mixtures to give the desired cephem ester (XXXVI) as a solid foam (184 mg., 59%).

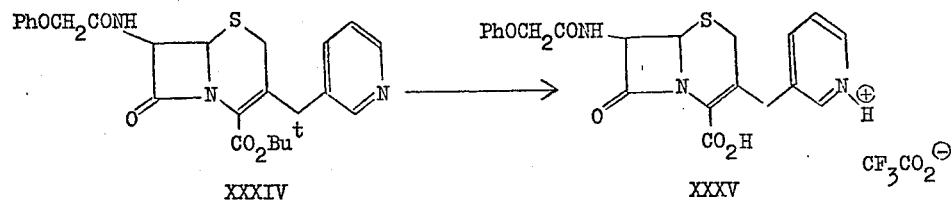

XXXIV → XXXV

The cephem ester (XXXIV) (100 mg.) was dissolved in trifluoroacetic acid (2 ml.) and kept at room temperature for 5 minutes. The solution was evaporated and the resulting gum was re-evaporated from dry toluene (4 × 1 ml.). The resulting gum was triturated with dry ether to give the desired trifluoroacetic acid salt (XXXV) as a solid (107 mg., 96%).

$\nu_{max}$ (KBr) 1775 cm$^{-1}$, 1675 cm$^{-1}$ (broad). $\lambda_{max}$ = 263 nm (ethanol) ε = 12,100 and $\lambda_{max}$ = 274 nm ε = 11,900 $\alpha_D^{23}$ = −35.9° (C=1% in ethanol).

The minimum inhibitory concentration (MIC) of this compound required to inhibit the growth of various bacteria on nutrient agar are tabulated below:

$\nu_{max}$ (CHCl$_3$) 1780 cm$^{-1}$, 1715 cm$^{-1}$, 1675 cm$^{-1}$.

δ ppm (CDCl$_3$) 1.26 (t, 3H, J=7Hz), 1.85 (s, 9H); 2.61 (q, 2H, J=7Hz); 3.10 and 3.51 (AB quartet, 2H, J=18Hz.); 3.97 (s, 2H); 3.49 and 4.15 (AB quartet, 2H, J=15Hz.); 5.07 (d, 1H, J=5Hz.); 5.87 (dd, 1H, J=5Hz, J'=9Hz); 7.10–8.8 (Aromatic multiplet + NH,5H). $\lambda_{max}$ = 263.5 nm (ethanol) ε = 12,000 $\alpha_D^{23}$= −88.7° (C=1% in chloroform). Molecular ion measured at 449.1435 C$_{21}$H$_{27}$N$_3$O$_4$S$_2$ requires 449.1443, Error = 1.8 ppm).

B. Preparation of 7β-ethylthioacetamido-3(3-pyridylmethyl)-3-cephem-4-carboxylic acid trifluoroacetic acid salt

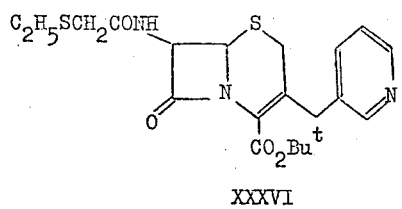
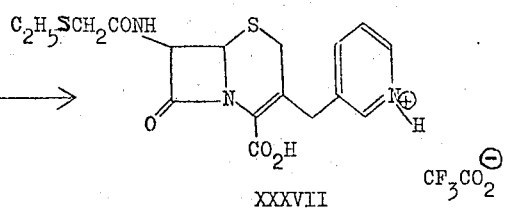

The cephem ester (XXXVI) (100 mg.) was dissolved in trifluoroacetic acid (2 ml.) and kept at room temperature for 5 minutes. The solution was evaporated and the resulting gum was re-evaporated from dry toluene (4 × 1 ml.). The resulting gum was triturated with dry ether to give the desired trifluoroacetic acid salt (XXXVII) as a solid (96 mg., 85%).

$\nu_{max}$ (KBr) 1775 cm$^{-1}$, 1670 cm$^{-1}$ (broad). $\lambda_{max}$ = 263 nm (ethanol) $\epsilon$ = 11,700. $\alpha_D{}^{23}$ = −22.8° (C=1% in ethanol).

The minimum inhibitory concentration (MIC) of this compound required to inhibit the growth of various bacteria on nutrient agar are tabulated below:

and the solid was washed with chloroform. The combined filtrates were washed with water, dried (MgSO$_4$), and evaporated to give a gum which on trituration with dry ether gave the desired cephem ester (XXXVIII) as a yellow solid (100 mg., 22%).

$\nu_{max}$ (CHCl$_3$) 1775 cm$^{-1}$, 1710 cm$^{-1}$, 1670 cm$^{-1}$. $\lambda_{max}$ = 263 nm (ethanol) $\epsilon$ = 10,000 $\alpha_D{}^{23}$ = −39.6° (C=1% in ethanol).

B. Preparation of 7β(Dα-guanidinophenylacetamido)-3(3-pyridylmethyl)-3-cephem-4-carboxylic acid di-trifluoroacetic acid salt.

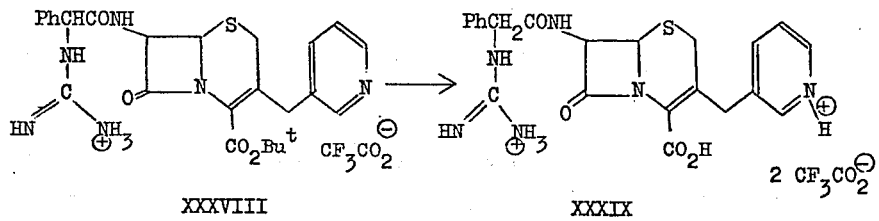

| Gram-positive bacteria | MIC (µg/ml) |
|---|---|
| *B. subtilis* | 0.5 |
| *Staph. aureus* Oxford | 0.05 |
| *Staph. aureus* Russell | 1.25 |
| β-Haemolytic Strep. CN 10 | 0.12 |
| *Strep pneumoniae* CN 33 | 0.25 |

| Gram-negative bacteria | MIC (µg/ml) |
|---|---|
| *E coli* NCTC 10418 | 50 |
| *Salmonella typhi* | 50 |
| *Shigella sonnei* | 50 |
| *Klebsiella aerogenes* A | 50 |
| *Proteus mirabilis* C 977 | 25 |

The cephem ester (XXXVIII) (60 mg.) was dissolved in trifluoroacetic acid (1 ml.) and kept at room temperature for 5 minutes. The solution was evaporated and the resulting gum was re-evaporated from dry toluene (3 × 0.5 ml.). The resulting gum was triturated with dry ether to give the desired di-trifluoroacetic acid salt (XXXIX) as a solid (51 mg., 79%).

$\nu_{max}$ (KBr) 1775 cm$^{-1}$, 1670 cm$^{-1}$ (broad).

The minimum inhibitory concentration (MIC) of this compound required to inhibit the growth of various bacteria on nutrient agar are tabulated below:

EXAMPLE 11

A. Preparation of tert-butyl 7β(Dα-guanidinophenylacetamido)-3(3-pyridylmethyl)-3-cephem-4-carboxylate trifluoroacetic acid salt

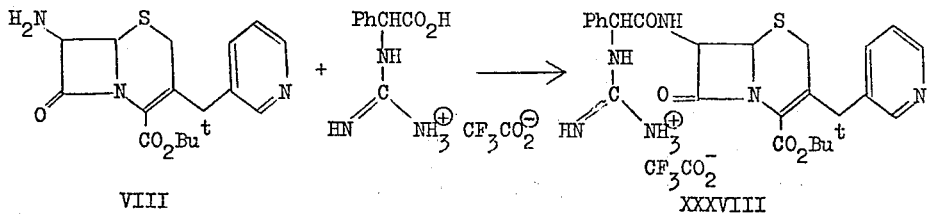

The free amine (VIII) (250 mg.) and Dα-guanidinophenylacetic acid trifluoroacetic acid salt (244 mg.) were dissolved in a mixture of dry methylene chloride (2 ml.) and dry dimethylformamide (1 ml.). The resulting mixture was stirred and cooled in a cold water bath and treated with a solution of dicyclohexylcarbodiimide (163 mg.) in dry methylene chloride (2 ml.). The mixture was stirred for 30 minutes followed by a further 30 minutes in an ice bath. The mixture was filtered

| Gram-positive bacteria | MIC (µg/ml) |
|---|---|
| *B. subtilis* | 2.5 |
| *Staph. aureus* Oxford | 0.5 |
| *Staph. aureus* Russell | 2.5 |
| β-Haemolytic Strep CN 10 | 0.1 |
| *Strep pneumoniae* CN 33 | 0.1 |

| Gram-negative bacteria | MIC (µg/ml) |
|---|---|
| *E coli* NCTC 10418 | >100 |
| *Salmonella typhi* | >100 |
| *Shigella sonnei* | >100 |
| *Klebsiella aerogenes* A | >100 |
| *Proteus mirabilis* C 977 | >100 |

EXAMPLE 12

A. Preparation of tert-butyl 7β(Dα-N-tert-butoxycarbonylamino-phenylacetamido)-3(3-pyridylmethyl)-3-cephem-4-carboxylate methiodide

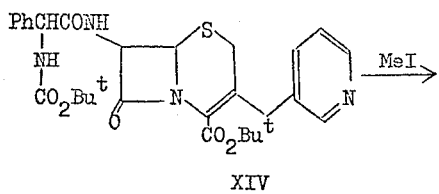 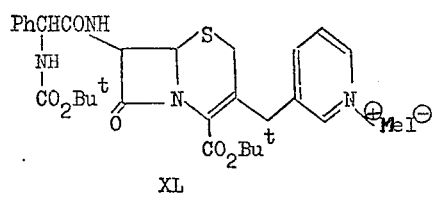

The cephem ester (XIV) (154 mg.) was dissolved in dry tetrahydrofuran (1 ml.) and treated with methyl iodide (0.2 ml.). The mixture was kept at room temperature for 16 hours. The mixture was diluted with dry ether and the resulting gum was triturated with dry ether to give the desired methiodide (XL) as a solid (178 mg., 93%).

$\nu_{max}$ (CHCl$_3$) 1785 cm$^{-1}$, 1710 cm$^{-1}$, 1690 cm$^{-1}$ (shoulder).

δ ppm (CDCl$_3$) 1.39 (s, 9H); 1.50 (s, 9H); 3.2–4.3 (broad m, 4H); 4.55 (s, 3H); 5.02 (d, 1H, J=5Hz); 5.34 (d, 1H, J=7Hz.); 5.6–6.0 (m, 2H); 7.40 (s, 5H); 7.7–8.2 (m, 2H); 8.35–8.75 (m, 1H); 8.8–9.35 (m, 2H);

$\lambda_{max}$ = 265 nm. (ethanol) ε = 14,300. $\alpha_D^{23}$ = −114.0° (C=1% in chloroform).

ethanol).

The minimum inhibitory concentration (MIC) of this compound required to inhibit the growth of various bacteria on nutrient agar are tabulated below:

| Gram-positive bacteria | MIC (μg/ml) |
|---|---|
| B. subtilis | 0.5 |
| Staph. aureus Oxford | 0.25 |
| Staph. aureus Russell | 12.5 |
| β-Haemolytic Strep. CN 10 | 0.05 |
| Strep. pneumoniae CN 33 | 0.25 |

| Gram-negative bacteria | MIC (μg/ml) |
|---|---|
| E coli NCTC 10418 | 50 |
| Salmonella typhi | 50 |
| Shigella sonnei | 50 |
| Klebsiella aerogenes A | 50 |
| Proteus mirabilis C 977 | 125 |

EXAMPLE 13

A. 4-t-Butoxycarbonyl-7-(2-t-butoxycarbonylamino-2-p-hydroxyphenylacetamido)-3-(3-pyridylmethyl)ceph-3-em

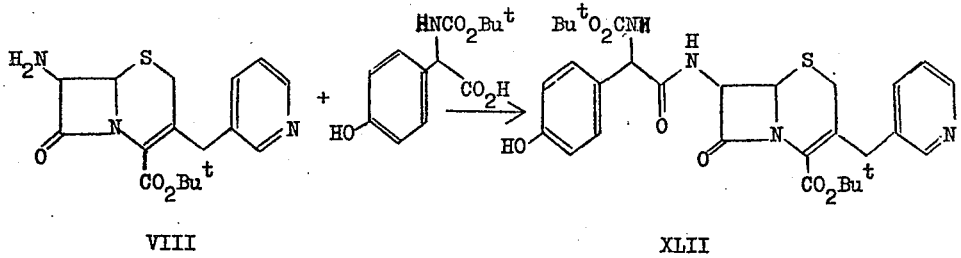

B. Preparation of 7β(Dα-aminophenylacetamido)-3(3-pyridylmethyl)-3-cephem-4-carboxylic acid metho-trifluoroacetate trifluoroacetic acid salt

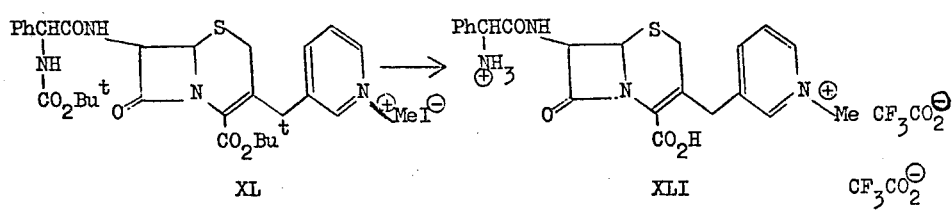

The methiodide (XL) (100 mg.) was dissolved in trifluoroacetic acid (2 ml.) and kept at room temperature for 10 minutes. The solution was evaporated to give a gum which was re-evaporated from dry toluene (4 × 1 ml.). The resulting gum was triturated with dry ether to give the desired trifluoroacetic acid salt (XLI) as a solid (93 mg., 100%).

$\nu_{max}$ (KBr) 1775 cm$^{-1}$, 1670 cm$^{-1}$ (broad). $\lambda_{max.}$ = 265 nm (ethanol) ε = 11,500. $\alpha_D^{23}$ = −27.7° (C=1% in N-t-Butoxycarbonyl-D-α-p-hydroxyphenylglycine (169 mg.), triethylamine (64 mg.) and dimethylbenzylamine (1 drop) were all dissolved in dry tetrahydrofuran (5 ml.). This solution was added dropwise over a period of 10 mins. to a solution of methyl chloroformate (60 mg.) in dry THF (5 ml.) that was being stirred in a solid CO$_2$ bath. After 20 mins., 7-amino-4-t-butoxycarbonyl-3-(3-pyridylmethyl)ceph-3-em (VIII) (200 mg.) in dry THF (5 ml.) was added dropwise and the reaction mixture was then stirred at −10° for 2 hours. The product was filtered and the filtrate concentrated to a yellow syrup which was chromatographed on silica gel 60 (<230 mesh) eluting with chloroform/methanol 19:1. The major product (XLII) was isolated as a pale yellow glass (140 mg. 41%);

$\nu_{max}$ (CHCl$_3$) 3400, 2970, 1780, 1720, 1620, 1600 and 1500 cm$^{-1}$;

δ ppm (CDCl$_3$) 1.41 (9H, s, Bu$^t$), 1.51 (9H, s, Bu$^t$), 2.87 and 3.33 (2H, ABq J=18Hz., S-CH$_2$-); 3.33 and 4.06 (2H, ABq J=15Hz., pyridyl CH$_2$); 4.92 (1H, d J=4.5Hz., lactam C6); 5.17 (1H, d J=6Hz.,

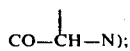

5.79 (1H, m, lactam C7); 5.87 (1H exchangeable, broad s OH); 6.73 (2H, d J=9Hz., phenyl); 7.19 (2H, d J=9Hz., phenyl); ca. 7.4 (1H, m, pyridyl C5), 7.75 (1H, d J=7Hz., pyridyl C4) and 8.37 (4H, broad, NH s and pyridyl C2 and C6).

B.
7-(2-Amino-2-p-hydroxyphenylacetamido)-4-carboxy-3-(3-pyridylmethyl) ceph-3-em bis-trifluoroacetic acid salt

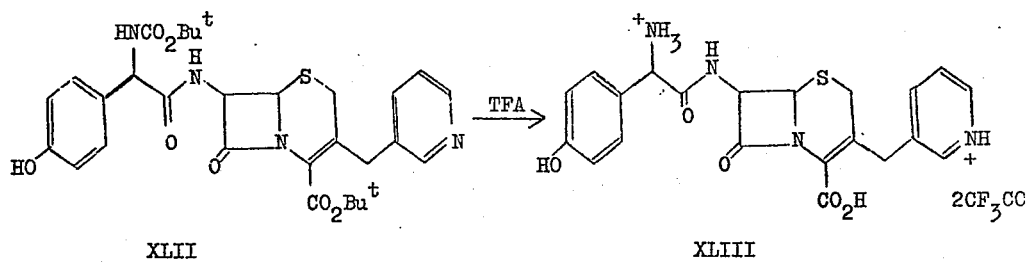

4-t-Butoxycarbonyl-7-(2-t-butoxycarbonylamino-2-p-hydroxyphenylacetamido)-3-(3-pyridylmethyl)ceph-3-em (XLII) (135 mg.) was dissolved in trifluoroacetic acid (2 ml.) and allowed to stand at room temperature for 15 mins. The excess trifluoroacetic acid was distilled off under reduced pressure and the final traces removed by evaporation with anhydrous toluene. The residue was triturated several times with dry ether to give the product (XLIII) as an off-white powder (115 mg., 76%);

$\nu_{max}$ (KBr) 3410, 3180, 3040. 2600, 1770, 1670 and 1515 cm$^{-1}$; $\lambda_{max}$ (EtOH) 229 nm (ε 15,100), 259 nm. (ε 10,400), 264 nm (ε 11,100) and 269 nm (ε 10,700); biochromatogram in butanol/ethanol/water 4:1:5 showed one zone of inhibition at R$_f$ 0.28.

The minimum inhibitory concentration (MIC) of this compound required to inhibit the growth of various bacteria on nutrient agar are tabulated below:

| Gram-positive bacteria | MIC (µg/ml) |
|---|---|
| B. subtilis | 0.25 |
| Staph aureus Oxford | 0.25 |
| Staph. aureus Russell | 2.5 |
| β-Haemolytic Strep. CN 10 | 0.12 |
| Strep. pneumoniae CN 33 | 0.12 |

| Gram-negative bacteria | MIC (µg/ml.) |
|---|---|
| E. coli NCTC 10418 | 5.0 |
| Salmonella typhi | 1.25 |
| Shigella sonnei | 5.00 |
| Klebsiella aerogenes A | 1.25 |
| Proteus mirabilis C 977 | 5.0 |

EXAMPLE 14

A.
4-t-Butoxycarbonyl-7-carboxymethylthioacetamido-3-(3-pyridylmethyl)ceph-3-em

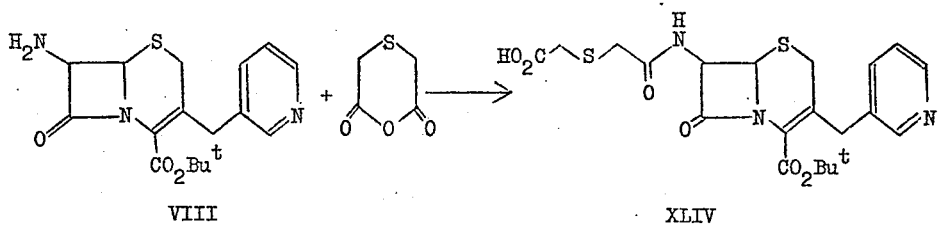

7-Amino-4-t-butoxycarbonyl-3-(3-pyridylmethyl)-ceph-3-em (VIII) (250 mg.) was dissolved in anhydrous methylene chloride (5 ml.) and cooled in an ice bath. It was treated with 1-oxa-4-thiacyclohexan-2,6-dione (95 mg.) and resulting solution was allowed to stand at room temperature for 3 hours. The solvent was stripped off and the residue was purified by chromatography on a short column of silica gel 60 (<230 mesh) eluting with chloroform/methanol 9:1. Trituration with ether gave the required acid (XLIV) as a non-crystalline powder (260 mg. 76%);

$\nu_{max}$ (CHCl$_3$) 3200 (broad), 2980, 2500 (broad), 1785, 1720, 1680 and 1515 cm$^{-1}$;

δppm (CDCl$_3$) 1.53 (9H, s, t-butyl); 2.9-3.8 (7H, m,

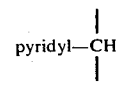

and —S—CH$_2$), 4.18 (1H, d J=15Hz.,

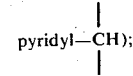

5.07 (1H, d J=4.5 Hz., lactam C6); 5.86 (1H, dd J=8 and 4.5 Hz., lactam C7); ca 7.4 (1H, m, pyridyl C5); 7.90 (1H, d J=7.5 Hz., pyridyl C4); 8.45 (1H exchangeable, d J=8Hz., NH); 8.58 (2H, broad, pyridyl C2 and C6) and 11.53 (1H, exchangeable, broad s CO₂H).

B.
4-Carboxy-7-carboxymethylthioacetamido-3-(3-pyridylmethyl)ceph-3-em trifluoroacetic acid salt

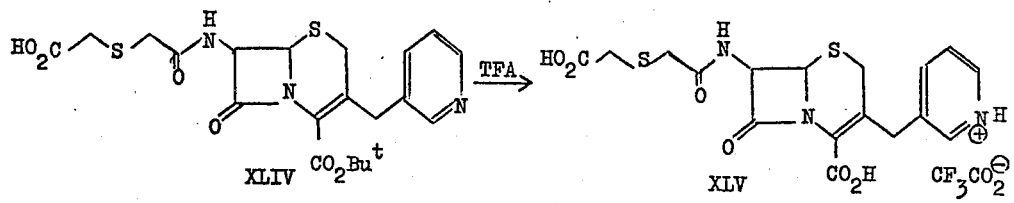

4-t-Butoxycarbonyl-7-carboxymethylthioacetamido-3-(3-pyridylmethyl)ceph-3-em (XLIV) (250 mg.) was dissolved in trifluoroacetic acid (3 ml.) and allowed to stand at room temperature for 15 mins. The trifluoroacetic acid was stripped off under reduced pressure and the last traces removed by additions of dry toluene and reevaporation. The residue was taken up in acetone (1 ml.) and the small amount of insoluble material discarded. The title compound (XLV) ws precipitated by careful addition of the acetone solution to dry ether (10 ml.). It was an off-white non-crystalline powder (150 mg., 54%);

$\lambda_{max}$ (nujol) 3300-2600 (broad), 1775, 1710, 1670, 1640 and 1545 cm⁻¹; $\epsilon_{max}$ (EtOH) 259 nm ($\epsilon$9,600), 264 nm. ($\epsilon$9,800) and 269 nm ($\epsilon$9,500);

δ ppm. (TFA) 3.5–5.0 (8H, m, S—CH₂S and pyridyl CH₂), 5.39 (1H, d J=4Hz., lactam C6), 5.96 (1H, dd J=8 and 4Hz., lactam C7); 8.0–8.4 (2H, m, pyridyl) and 8.6–9.0 (3H, m, pyridyl and NH); biochromatogram in butanol/acetic acid/water 12:3:5 showed one zone of inhibition at R_f 0.24.

The minimum inhibitory concentration (MIC) of this compound required to inhibit the growth of various bacteria on nutrient agar are tabulated below:

| Gram-positive bacteria | MIC (μg/ml) |
|---|---|
| B. subtilis | 25 |
| Staph. aureus Oxford | 1.25 |
| Staph. aureus Russell | 12.5 |
| β-Haemolytic Strep. CN 10 | 5.0 |
| Strep. pneumoniae CN 33 | 12.5 |

| Gram-negative bacteria | MIC (μg/ml) |
|---|---|
| E coli NCTC 10418 | 50 |
| Salmonella typhi | 50 |
| Shigella sonnei | 50 |
| Klebsiella aerogenes A | 25 |
| Proteus mirabilis C 977 | 50 |

EXAMPLE 15

A. Preparation of tert-Butyl 7-β-[(dl)-α-tert-Butyloxycarbonylamino-2-thienylacetamido]-3-(3-pyridylmethyl)-3-cephem-4-carboxylate

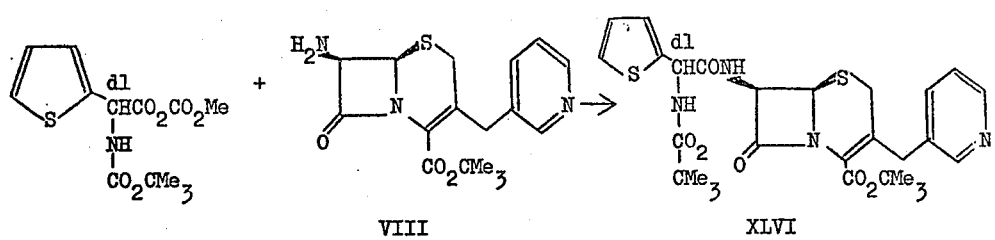

(dl)-α-tert-Butyloxycarbonylamino-2-thienylacetic acid (163 mg.), triethylamine (64 mg.) and dimethylbenzylamine (1 drop) in tetrahydrofuran (4 ml.) were added dropwise to methyl chloroformate (60 mg). in tetrahydrofuran at −30° to −40°. The mixture was stirred at −30° for 30 minutes. tert-Butyl 7-β-amino-3-(3-pyridylmethyl)-3-cephem-4-carboxylate (VIII) (200 mg.) in tetrahydrofuran (3 ml.) was then added to the mixture at −30°. The mixture was cooled to −70° and then allowed to warm to −30° over 1 hr. The solvent was then removed and the residue chromatographed on silica gel, eluting with dichloromethane, followed by a 1:1 mixture of ethyl acetate and petroleum ether (b.p. 60°–80°) to give the acylated cephem (206 mg.). This was rechromatographed on silica gel, eluting with chloroform to give tert-butyl 7-β- [(dl)-α-tert-butyloxycarbonylamino-2-thienylacetamido]-3-pyridylmethyl)-3-cephem-4-carboxylate (XLVI) (180 mg.) as an amorphous solid. Found: M⁺ m/e 586.1925: $C_{28}H_{34}N_4O_6S_2$ requires M⁺ m/e 586.1920 (error 0.85 ppm).

$\lambda_{max}$ (EtOH) 240 nm ($\epsilon_{max}$ 14,600) and 263 nm ($\epsilon_{max}$ 11,500). $\nu_{max}$ (CH₂CL₂) 3420, 1785, 1720 and 1705 (sh) cm⁻¹.

δ ppm (CDCl₃) 1.47 (s) and 1.58(s) (total 18H), 2.82 and 3.37 (ABq., J=20Hz.), 3.28 and 4.08 (ABq., J=14Hz.) (total for 2 quartets 4H), 5.02 (broadened d, J=5Hz., 1H), 5.55–6.20 (m, 3H), 6.85–7.45 (m, 4H), 7.78 (d, J=7Hz., 1H), 8.48 (broad s, 3H).

B. Preparation of 7-β-[(dl)-α-Amino-2-thienylacetamido]-3-(3-pyridylmethyl)-3-cephem-4-carboxylic acid Di-trifluoroacetic acid salt

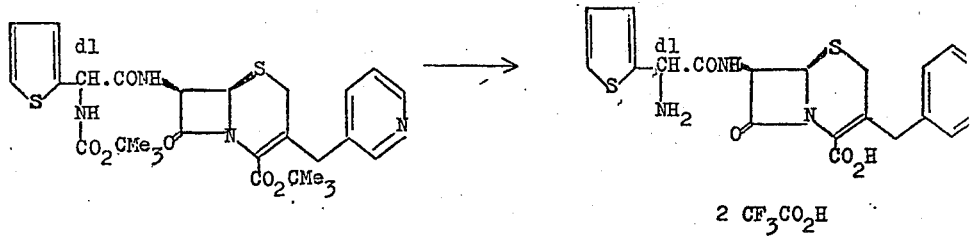

tert-Butyl 7-β-[(dl)-α-tert-butyloxycarbonylamino-2-thienylacetamido]-3-(3-pyridylmethyl)-3-cephem-4-carboxylate (XLVl) (150mg) was dissolved in trifluoroacetic acid for 15-20 minutes at room temperature.

EXAMPLE 16

A. Preparation of tert-butyl 7β-(4-pyridylthioacetamido)-3(3-pyridylmethyl)-3-cephem-4-carboxylate.

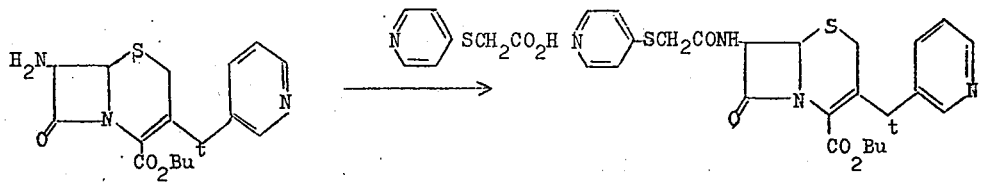

The trifluoroacetic acid was removed under reduced pressure, toluene was added to the residue and evaporated off (2X). The residue was then triturated with ether to give 7-β-[(dl)-α-amino-2-thienylacetamido]-3-pyridylmethyl)-3-cephem-4-carboxylic acid di-trifluoroacetic acid salt (XLVll) as a colourless solid. λmax (EtOH) 240nm. (εmax 11,600) and 263nm. (εmax 9200). $\nu_{max}$ (KBr) 3410, 1775 and 1765 cm$^{-1}$.

The minimum inhibitory concentration (MIC) of this compound required to inhibit the growth of various bacteria on nutrient agar are tabulated below:

| Gram-positive bacteria | MIC(μg/ml) |
|---|---|
| B. subtilis | 1.25 |
| Staph. aureus Oxford | 0.5 |
| Staph. aureus Russell | 5.0 |
| β-Haemolytic Strep CN10 | 0.5 |

| Gram-negative bacteria | MIC(μg/ml) |
|---|---|
| E coli JT 1 | 12.5 |
| Salmonella typhi | 2.5 |
| Shigella sonnei | 5.0 |
| Klebsiella aerogenes A | 5.0 |
| Proteus mirabilis C977 | 12.5 |

By replacing the dl-starting acid in part A above with the corresponding d-starting acid the given procedure produces the D-cephem.

To a solution of the free base (Vlll) (250mg) in dry methylene chloride (1ml) at room temperature, was added dicyclohexylcarbodiimide (149mg) in methylene chloride (1ml) followed by 4-pyridylthioacetic acid hydrobromide (180 mg) in dimethyl formamide (2ml) dropwise, was stirring, over 2 minutes. After stirring the mixture for 30 minutes, surrounded by a water bath, and, for a further 30 minutes, surrounded by an ice bath, the white solid, which had precipitated, was filtered off, and the filtrate diluted with ethyl acetate, washed with aqueous sodium bicarbonate, brine dried and evaporated. The residue was chromatographed on silica gel, eluting with chloroform/methanol mixtures, to give the desired cephem ester (XLVlll) (160mg) as a solid. $\nu_{max}$ (CHCl$_3$) 1785, 1718, 1685 cm$^{-1}$; λ$_{max}$ = 265nm (ethanol) ε$_{max}$ = 14,320 α$_D^{24}$ = − 12.8°(c = 1% in chloroform). Molecular ion measured at 498.1377 (C$_{24}$H$_{26}$O$_4$N$_4$S$_2$ requires 498.1395. Error 3.6 ppm.).

δppm (CDCl$_3$): 1.53(s,9H); 2.97 and 3.44 (AB quartet, 2H, J = 19Hz); 3.41 and 4.09 (AB quartet, 2H, J = 14Hz); 3.83 (s, 2H); 5.00 (d, 1H, J = 4.5Hz); 5.85 (d,d,1H, J = 4.5Hz, J$^1$ = 9Hz, collapsing to d, J = 4.5Hz with D$_2$O): 7.16–7.83 (m,4H); 8.31 (d, 1H, J = 9Hz, exchanging with D$_2$O); 8.40 – 8.67 (m, 4H).

B. Preparation of 7β(4-pyridylthioacetamido)-3(3-pyridylmethyl)-3-cephem-4-carboxylic acid di-trifluoroacetic acid salt

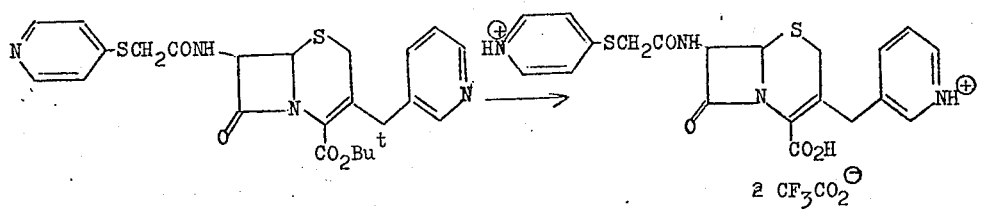

The cephem ester (XLVlll) (89mg) was dissolved in trifluoroacetic acid (2ml) and kept at room temperature for 5 minutes. The solution was diluted with dry toluene and evaporated (x2). Trituration of the residual gum with dry ether gave the desired cephem di-trifluoroacetic acid salt (IL) (60mg) as a solid. $\nu_{max}$ (KBr) 1775, 1670 (broad) cm$^{-1}$ $\lambda_{max}$ = 263nm (ethanol) $\epsilon_{max}$ = 13,320 $\alpha_D{}^{24}$ = +12.8° (c=1% in ethanol).

The minimum inhibitory concentration (MIC) of this compound, required to inhibit the growth of various bacteria on nutrient agar are tabulated below:

| Gram-positive bacteria | MIC($\mu$g/ml) |
|---|---|
| B. subtilis | <0.02 |
| Staph. aureus Oxford | <0.02 |
| Staph. aureus Russell | 1.0 |
| β-Haemolytic Strep CN10 | <0.02 |
| Strep. pneumoniae CN 33 | <0.02 |

| Gram-negative bacteria | MIC($\mu$g/ml) |
|---|---|
| E coli NCTC 10418 | 25 |
| Salmonella typhi | 10 |
| Shigella sonnei | 25 |
| Klebsiella aerogenes A | 5.0 |
| Proteus mirabilis C 977 | 100 |

EXAMPLE 17

A. Preparation of tert-butyl 7β(4-pyridylacetamido)-3(3-pyridylmethyl)-3-cephem-4-carboxylate

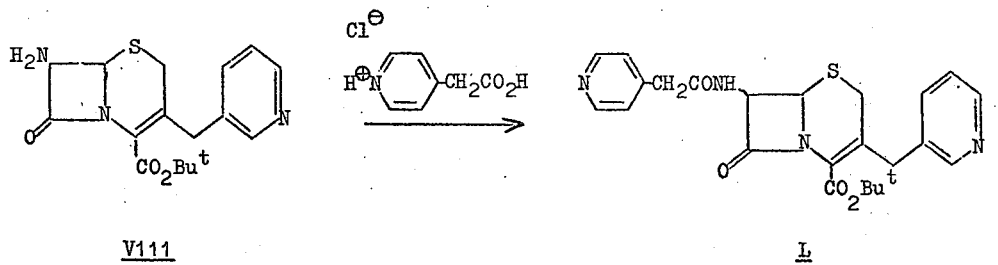

V111      L

To a solution of the free base (V111) (250mg) in dry methylene chloride (1ml), at room temperature, was added dicyclohexyl carbodiimide (149mg) in methylene chloride (1ml) followed by 4-pyridylacetic acid hydrochloride (125mg) in dimethylformamide (2ml), dropwise, with stirring, over about 2 minutes. After stirring the mixture, for 30 minutes, surrounded by a water bath, and, for a further 30 minutes, surrounded by an ice bath, the white solid which had precipitated, was filtered off. The filtrate was diluted with ethyl acetate, washed with aqueous sodium bicarbonate, then brine, dried (MgSO$_4$), and evaporated. Chromatography of the residue on silica gel, eluting with chloroform/methanol mixtures gave the desired cephem ester (L) (76mg), as a solid foam. $\nu_{max}$ (CHCl$_3$) 1780, 1715, 1685 cm$^{-1}$ $\lambda_{max}$ = 263.5nm (ethanol) $\epsilon_{max}$ = 10,140. Molecular ion measured at 466.1671 (C$_{24}$H$_{26}$O$_4$SN$_4$ requires 466.1675. Error 0.9 ppm) δppm (CDCl$_3$): 1.52 (s, 9H); 300 and 3.45 (AB quartet, 2H, J= 18Hz); 3.41 and 4.09 (AB quartet, 2H, J=15Hz); 3.66 (s, 2H); 5.01 (d, 1H, J = 4.5Hz; on 7.89 94 8.5. H). 5.87 (d,d, 1H, J = 4.5Hz, J$^1$ = 8.5Hz, collapsing to d, j = 4.5Hz on D$_2$O shake); 7.15 –]7.76 (m, 4H); 7.89 (d, 1H, J = 8.5Hz, exchanging with D$_2$O); 8.35 – 8.65 (m, 4H).

B. Preparation of 7β(4-pyridylacetamido)-3(3-pyridylmethyl)-3-cephem-4-carboxylic acid di-trifluoroacetic acid salt

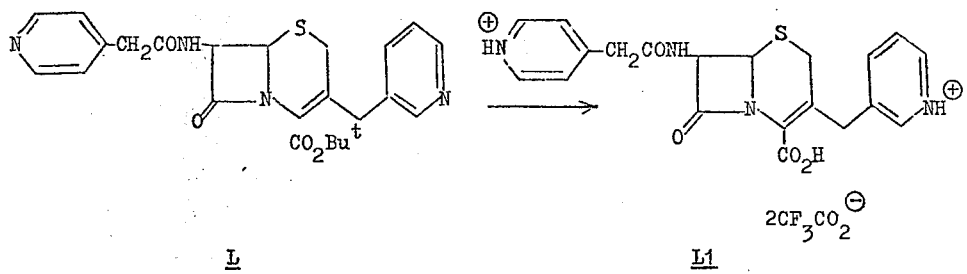

L      L1

The cephem ester (L) (63mg) was dissolved in trifluoroacetic acid (2ml). After allowing to stand at room temperature for about 10 minutes the solution was diluted with dry toluene and evaporated to dryness (×2). Trituration of the residual gum with dry ether gave the desired cephem ditrifluoroacetic acid salt (L1) (60mg) as a solid.

$\nu_{max}$ (KBr) 1775, 1670 (broad) cm$^{-1}$ $\lambda_{max}$ = 262.5nm (ethanol) $\epsilon_{max}$ = 9,600 $\alpha_D$ = − 25° (c= 1% in ethanol)

The minimum inhibitory concentration (MIC) of this compound, required to inhibit the growth of various bacteria on nutrient agar are tabulated below:

| Gram-positive bacteria | MIC($\mu$g/ml) |
|---|---|
| B. subtilis | 0.25 |
| Staph.aureus Oxford | 0.12 |
| Staph.aureus Russell | 25 |
| β-Haemolytic Strep CN10 | 0.12 |

| Gram-negative bacteria | MIC($\mu$g/ml) |
|---|---|
| Ecoli JT 1 | 25 |
| Salmonella typhi | 10 |
| Shigella sonnei | 25 |
| Klebsiella aerogenes A | 10 |
| Proteus mirabilis C 977 | 10 |

EXAMPLE 18

A. Preparation of tert-butyl 7β-(DL-3-[cyclohex-3-ene]-3-tert-butoxycarbonylaminopropionamido)-33(3pyridylmethyl)-3cephem-4-carboxylate

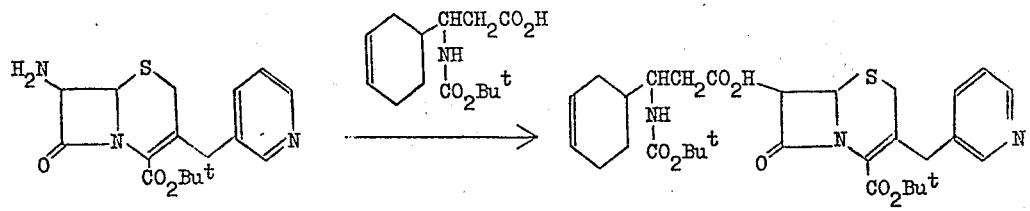

To a solution of methyl chloroformate (61 mg.) in dry tetrahydrofuran (5 ml.) at −10°, was added, dropwise, with stirring, over a period of 5 minutes, a solution containing DL-3-(cyclohex-3-ene)-3-tert-butoxycarbonylamino-propionic acid (172 mg.), dry triethylamine (59 mg.) and N,N-dimethylbenzylamine (1 drop) in dry tetrahydrofuran (2.5 ml.). After stirring the mixture for a further 15 minutes at −10°, the free amino (VIII) (204 mg.) in dry tetrahydrofuran (2.5 ml.) was added, dropwise, and the resulting mixture stirred for a further hour at −10° to 0°C. The mixture was filtered and the filtrate evaporated to give a gum, which was dissolved in ethyl acetate and washed with water, dilute hydrochloric acid, water, aqueous sodium bicarbonate, then brine, dried (MgSO$_4$) and evaporated. Chromatography of the residue on silica gel, eluting with chloroform, gave the desired cephem ester (LII) (80 mg.) as a solid foam.

$\nu_{max}$ (CHCl$_3$) 1780, 1710 (broad) cm$^{-1}$. $\lambda_{max}$ = 264 nm (ethanol) $\epsilon_{max}$ = 9,250 and $\lambda_{max}$ = 269.5 nm (ethanol) $\epsilon_{max}$ = 9,150. Molecular ion measured at 598.2815 (C$_{31}$H$_{42}$O$_6$N$_4$S requires 598.2825, Error 1.7 ppm).

B. Preparation of 7β-(DL-3-[cyclohex-3-ene]-3-aminopropionamido)-3(3-pyridylmethyl)-3-cephem-4-carboxylic acid di-trifluoroacetic acid salt

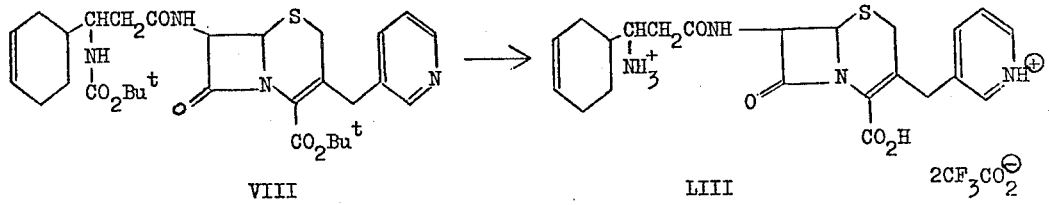

The cephem ester (LII) (70 mg.) was dissolved in trifluoroacetic acid (2ml.). After leaving the solution at room temperature for 10 minutes, it was diluted with dry toluene and evaporated to dryness. Re-evaporation from toluene, and triturating the residual gum with dry ether gave the desired cephem di-trifluoroacetic acid salt (LIII) (73 mg.) as a solid. $\nu_{max}$ (KBr) 1775, 1670 (broad) cm$^{-1}$ $\lambda_{max}$ = 263.5 nm (ethanol) $\epsilon_{max}$ = 9,550 and $\lambda_{max}$ = 269 nm (ethanol) $\epsilon_{max}$ = 9,290.

The minimum inhibitory concentration (MIC) of this compound required to inhibit the growth of various bacteria on nutrient agar are tabulated below:

| Gram-positive bacteria | MIC (μg/ml) |
| --- | --- |
| B. subtilis | 1.25 |
| Staph. aureus Oxford | 0.5 |
| Staph. aureus Russell | 1.25 |
| β-Haemolytic Strep. CN 10 | 0.5 |

| Gram-negative bacteria | MIC (μg/ml) |
| --- | --- |
| E coli JT 1 | 125 |
| Salmonella typhi | 125 |
| Shigella sonnei | 125 |
| Klebsiella aerogenes A | 125 |
| Proteus mirabilis C 977 | 250 |

EXAMPLE 19

A. Preparation of tert-butyl 7β-(DL-α-tert-butoxycarbonyl aminocyclopropylacetamido)-3(3-pyridylmethyl)-3-cephem-4-carboxylate

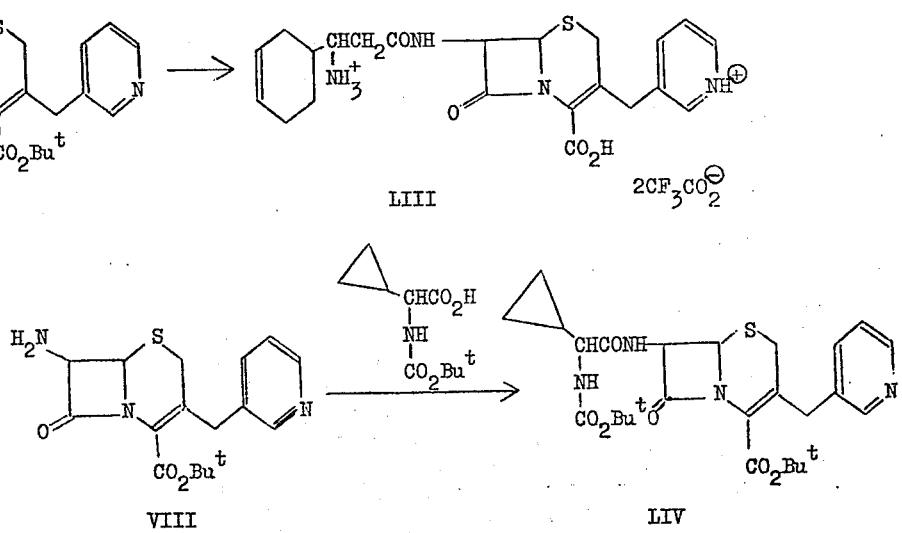

To a solution of methylchloroformate (69 mg.) dry tetrahydrofuran (5ml.) at −10°, was added, dropwise, with stirring, a solution containing N(-tert-butoxycarbonyl)-DL-α-amino cyclopropyl acetic acid (157 mg.), dry triethylamine (74 mg.) and N,N-dimethylbenzylamine (1 drop) in dry tetrahydrofuran (2.5 ml.). After stirring the mixture at −10° for 15 minutes, the free amine (VIII) (230 mg.) in dry tetrahydrofuran (2.5 ml.) was added dropwise and the resulting mixture stirred for a further hour at this temperature. The mixture was filtered and the filtrate evaporated to give a gum, which was taken up in ethyl acetate, washed with aqueous sodium bicarbonate, then brine, dried (MgSO₄) and evaporated. Silica gel chromatography of the residue, eluting with chloroform gave the desired cephem ester (LIV) (200 mg.) as a solid foam.

$\nu_{max}$ (CHCl₃) 1780, 1710, 1692 (shoulder), 1682 (shoulder) cm$^{-1}$. $\lambda_{max}$ = 263.7 nm (ethanol) $\epsilon_{max}$ = 10,430 and $\lambda_{max}$ = 269 nm (ethanol) $\epsilon_{max}$ = 10,230. Molecular ion measured at 544.2331 ($C_{27}H_{36}O_6SN_4$ requires 544.2355, Error 4.8 ppm).

B. Preparation of 7β-(DL-α-aminocyclopropylacetamido)-3(3-pyridylmethyl)-3-cephem-4-carboxylic acid di-trifluoroacetic acid salt

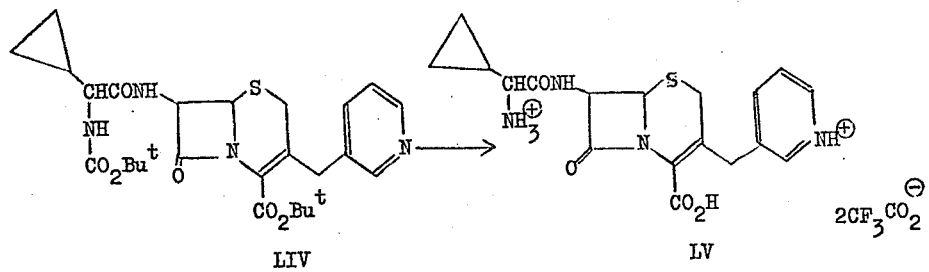

The cephem ester (LIV) (160 mg.) was dissolved in trifluoroacetic acid (2 ml.). After standing the solution at room temperature for 10 mins., it was diluted with dry toluene and evaporated to dryness. The residue was re-evaporated from toluene and then triturated with dry ether to give the desired cephem di-trifluoroacetic acid salt (LV) (150 mg.) as a solid.

$\nu_{max}$ (KBr) 1775, 1675 (broad) cm$^{-1}$. $\lambda_{max}$ = 263.5 nm (ethanol) $\epsilon_{max}$ = 9,630, and $\lambda_{max}$ = 269.5 nm (ethanol) $\epsilon_{max}$ = 9,345.

The minimum inhibitory concentration (MIC) of this compound required to inhibit the growth of various bacteria on nutrient agar are tabulated below:

| Gram-positive bacteria | MIC (µg/ml) |
|---|---|
| B. subtilis | 12.5 |
| Staph. aureus Oxford | 5.0 |
| Staph. aureus Russell | 12.5 |
| β-Haemolytic Strep. CN 10 | 2.5 |

| Gram-negative bacteria | MIC (µg/ml) |
|---|---|
| E coli JT 1 | 500 |
| Salmonella typhi | 250 |
| Shigella sonnei | 250 |
| Klebsiella aerogenes A | 250 |
| Proteus mirabilis C 977 | 500 |

EXAMPLE 20

7β-[D-2-(Cinnamylmethylureido)phenylacetamido]-3-(3-pyridylmethyl)-3-cephem-4-carboxylic acid

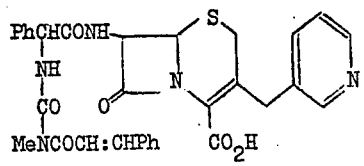

LVI

7β(-D-α-Aminophenylacetamido)-3(3-pyridylmethyl)-3-cephem-4-carboxylic acid di-trifluoroacetic acid salt (XV) (300 mg. 1 eq.) in methylene chloride (10 ml.) containing triethylamine (0.2 g. 4.4 eq.) was treated with N-chlorocarbonyl-N-methyl cinnamide (0.113 g., 1.1 eq.) in methylene chloride (5 ml.) at room temperature for 3 hr. The total product after removal of the solvent was gum which on trituration with water gave the title compound (LVI) as a brown solid (150 mg.) after drying in vacuo.

$\nu_{max}$ (KBr dis.) 3600–3200, 1770, 1660, 1610 cm$^{-1}$.

The minimum inhibitory concentraion (MIC) of this compound required to inhibit the growth of various bacteria on nutrient agar are tabulateed below:

| Gram-positive bacteria | MIC (µg/ml) |
|---|---|
| B. subtilis | 32 |
| Staph. aureus Oxford | 4 |
| Staph. aureus Russell | 63 |
| β-Haemolytic Strep. CN 10 | 0.25 |

| Gram-negative bacteria | MIC (µg/ml) |
|---|---|
| E coli JT 1 | 125 |
| Salmonella typhi | >125 |
| Shigella sonnei | 63 |
| Klebsiella aerogenes | 63 |
| Proteus mirabilis C 977 | >125 |

EXAMPLE 21

7β-[α(3-Benzylideneimino-3-methylureido)-phenylacetamido]-3(3-pyridylmethyl)ceph-3em-4-carboxylic acid

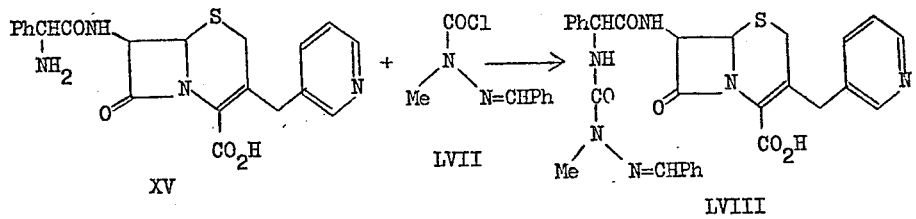

The cephem (XV) (266 mg., as the di-trifluoroacetic acid salt) in methylene chloride (10 ml.), was cooled in an ice-bath. Triethylamine (182 mg.) was added, followed by the N-carbonyl chloride (LVII) (88 mg.) in methylene chloride (2 ml.). The reaction mixture was left at room temperature for 3½ hours, and then evaporated to dryness. The residue, after washing with ether and water gave the product (LVIII) as a buff solid from chloroform-ether (140 mg.).

$\nu_{max}$ (CHCl$_3$) 3400, 3300, 1780, 1680 (b), 1610 cm$^{-1}$.

EXAMPLE 22

Following the general procedure of Example 2 for converting the trifluoroacetic acid salt of 3 (3-pyridylmethyl)-7β-(2-thienylacetamido-3-cephem-4-carboxylic acid to the free acid, the trifluoroacetic acid salts of Examples 3B, 4B, 6B, 7b, 8B, 9B, 10B, 11B, 12B, 13B, 14B, 15B, 16B, 17B and 18B are each converted to the corresponding free acid.

We claim:

1. A 7-β-acylamino-ceph-3-em compound of the formula (II):

(structure II)

or a pharmaceutically acceptable acid addition salt thereof, wherein

Py is 2-pyridyl or 3-pyridyl,

R$^1$ is COOH, a salt of COOH selected from the sodium, potassium, calcium, magnesium, aluminum, triethylamine, procaine, dibenzylamine, triethanolamine, 1-ephenamine and ethylpiperidine or a hydrolyzable ester which breaks down in the body to the free acid selected from acetoxymethyl, pivaloyloxymethyl, α-acetoxymethyl, α-acetoxybenzyl, α-pivaloyloxyethyl, phthalide, and 3,4 dimethyl phthalide R is $$R^2(CH_2)_n-\underset{X}{CH}-(CH_2)_m-CO- \quad (i)$$

in which

R$^2$ is hydrogen, lower alkyl, C$_{3-6}$ cycloalkyl, cyclohexenyl, cyclohexadienyl, phenyl, p-hydroxyphenyl, thienyl, pyridyl, isoxazolyl, 3-O-chlorophenyl-5-methyl-isoxazol-4-yl, sydnonyl or tetrazolyl, X is hydrogen, hydroxy, halogen, COOH or its phenyl or indanyl ester, azido, amino, ureido, guanidino, triazolyl, tetrazolyl, cyano, formyloxy, lower alkanoyloxy or lower alkoxy; and n and m are each 0, 1, 2 or 3; or (structure ii)

in which n is 1, 2, 3 or 4 and X is as defined in (i) above, or $$R^4-Z-\underset{R^6}{\overset{R^5}{C}}-CO \quad (iii)$$

in which

R$^4$ is lower alkyl, benzyl, phenyl, C$_{3-6}$ cycloalkyl, cyclohexenyl, cyclohexadienyl, thienyl or pyridyl, R$^5$ and R$^6$ are each hydrogen, lower alkyl, phenyl, benzyl or phenylethyl, and Z is oxygen or sulphur.

2. A compound of claim 1 wherein the acid addition salt is the sulphate, nitrate, phosphate, borate, hydrochloride, hydrobromide, hydroiodide, acetate, tartrate, malate, citrate, succinate, benzoate, ascorbate, or methanesulphonate.

3. 7β-(D-α-aminophenylacetamido)-3(3-pyridylmethyl)-3-cephem-4-carboxylic acid.

4. 7β-(D-2-amino-2-p-hydroxyphenylacetamido)-4-carboxy-3-(3-pyridylmethyl)ceph-3-em.

5. 7β-(DL-α-amino-2-thienylacetamido)-3-(3-pyridylmethyl)-3-cephem-4-carboxylic acid.

6. 7β-(D-α-amino-2-thienylacetamido)-3-(3-pyridylmethyl)-3-cephem-4-carboxylic acid.

7. 7β-(D-α-hydroxyphenylacetamido)-3(3-pyridylmethyl)-3-cephem-4-carboxylic acid.

8. A pharmaceutically acceptable salt of a compound selected from the group 7β-(D-α-aminophenylacetamido)-3-(3-pyridylmethyl)-3-cephem-4-carboxylic acid, 7β-(D-2-amino-2-p-hydroxyphenylacetamido)-4-carboxy-3-(3-pyridylmethyl)-ceph-3-em, 7β-(DL-α-amino-2-thienylacetamido)-3-(3-pyridylmethyl)-3-cephem-4-carboxylic acid, 7β-(D-α-amino-2-thienylacetamido)-3-(3-pyridylmethyl)-3-cephem-4-carboxylic acid, 7β-(D-α-hydroxyphenylacetamido)-3-(3-pyridylmethyl)-3-cephem-4-carboxylic acid.

9. A pharmaceutically acceptable ester of a compound selected from the group 7β-(D-α-aminophenylacetamido)-3-(3-pyridylmethyl)-3-cephem-4-carboxylic acid, 7β-(D-2-amino-2-p-hydroxyphenylacetamido)-4-carboxy-3-(3-pyridylmethyl)-ceph-3-em, 7β-(DL-α-amino-2-thienylacetamido)-3-(3-pyridylmethyl-3-cephem-4-carboxylic acid, 7β-(D-α-amino-2-thienylacetamido)-3-(3-pyridylmethyl)-3-cephem-4-carboxylic acid, 7β-(D-α-hydroxyphenylacetamido)-3-(3-pyridylmethyl)-3-cephem-4-carboxylic acid, said ester being a hydrolyzable ester which breaks down in the body to the free acid and selected from acetoxymethyl, pivaloyloxymethyl, α-acetoxyethyl, α-acetoxybenzyl, α-pivaloyloxyethyl, phthalide and 3,4 dimethylphthalide.

* * * * *

UNITED STATES PATENT AND TRADEMARK OFFICE
CERTIFICATE OF CORRECTION

PATENT NO. : 3,966,718
DATED : June 29, 1976
INVENTOR(S) : Edward George Brain et al It is certified that error appears in the above—identified patent and that said Letters Patent are hereby corrected as shown below:

In the heading     "2561/73" should read

--2571/73

October 20, 1973 - 49000/73--

*Signed and Sealed this*

Twenty-eighth *Day of* September 1976

[SEAL]

*Attest:*

RUTH C. MASON
*Attesting Officer*

C. MARSHALL DANN
*Commissioner of Patents and Trademarks*